United States Patent
Paloni

(10) Patent No.: US 12,303,583 B2
(45) Date of Patent: May 20, 2025

(54) COMPOSITIONS AND METHOD OF USE FOR HAIR STRAIGHTENING AND SHAPING

(71) Applicant: Olaplex, Inc., Santa Barbara, CA (US)

(72) Inventor: Justin Paloni, Cambridge, MA (US)

(73) Assignee: OLAPLEX, INC., Santa Barbara, CA (US)

( * ) Notice: Subject to any disclaimer, the term of this patent is extended or adjusted under 35 U.S.C. 154(b) by 0 days.

(21) Appl. No.: 17/981,446

(22) Filed: Nov. 6, 2022

(65) Prior Publication Data

US 2024/0207161 A1   Jun. 27, 2024

Related U.S. Application Data

(63) Continuation of application No. 17/555,392, filed on Dec. 18, 2021, now Pat. No. 11,596,589.

(60) Provisional application No. 63/205,666, filed on Dec. 19, 2020.

(51) Int. Cl.
| | |
|---|---|
| A61K 8/64 | (2006.01) |
| A61Q 5/04 | (2006.01) |
| C07K 7/06 | (2006.01) |
| C07K 9/00 | (2006.01) |
| C07K 14/47 | (2006.01) |

(52) U.S. Cl.
CPC ............ *A61K 8/64* (2013.01); *A61Q 5/04* (2013.01); *C07K 7/06* (2013.01); *C07K 9/001* (2013.01); *C07K 14/47* (2013.01)

(58) Field of Classification Search
None
See application file for complete search history.

(56) References Cited

U.S. PATENT DOCUMENTS

| | | | |
|---|---|---|---|
| 4,935,231 | A | 6/1990 | Pigiet |
| 10,709,655 | B2 | 7/2020 | Cavaco Paulo |
| 11,596,589 | B2 | 3/2023 | Paloni |
| 2011/0214206 | A1 | 9/2011 | La Rosa |
| 2012/0052034 | A1 | 3/2012 | Azizova |
| 2014/0093473 | A1 | 4/2014 | Hauser |
| 2016/0199513 | A1 | 7/2016 | Bancel |
| 2019/0314260 | A1 | 10/2019 | Olsen |

FOREIGN PATENT DOCUMENTS

| | | |
|---|---|---|
| EP | 1431306 | 6/2004 |
| WO | 02081649 | 10/2002 |
| WO | 03008625 | 1/2003 |
| WO | 2004024173 | 3/2004 |
| WO | 2006078161 | 7/2006 |
| WO | 2007136286 | 11/2007 |
| WO | 2009041739 | 4/2009 |
| WO | 2009108713 | 9/2009 |
| WO | 2011043333 | 4/2011 |
| WO | 2013151665 | 10/2013 |
| WO | 2014104981 | 7/2014 |
| WO | 2015056216 | 4/2015 |
| WO | 2020031150 | 2/2020 |
| WO | 2021260667 | 12/2021 |

OTHER PUBLICATIONS

ISR PCT/US2021/064245 mailed Jul. 25, 2022.
Azoia, et al., "Molecular modeling of hair keratin/peptide complex: Using MM-PBSA calculations to describe experimental binding results", Proteins, 1409-1417 (2012).
Cruz, et al., Changing the shape of hair with keratin pepetides, RSC Advances, 7:51581-51592 (2017a).
Cruz, et al., Peptide-protein interactions within human hair keratins, Int. J. of Biological Macromolecules, 101:805-814 (2017b).
Dong-Dong, et al., Molecular Evolution of the Keratin Associated Protein Gene Family in Mammals, Role in the Evolution of Mammalian Hair, BMC Evolutionary Biology, Biomed. Central LRT, 8(1):231 (2008).
Evans, "Astatistical analysis of harirbreakage. II repeated grooming experiments", J. Cosmet. Sci., 61:439-455 (2010).
Feng, et al., "Complementary Roles of Specific Cysteines in Keratin 14 toward the Assembly, Organization, and Dynamics of Intermediate Filaments in Skin Keratinocytes", Journal of Biological Chemistry, 290(3):22507-22519 (2015).
Nakamura, et al., "Rapid extraction procedure of human hair proteins and identification of phosphorylated species", biol. Pharm. Bull., 25(5):569-572 (2002).
Yampolsky, et al., "The exchangeability of amino acids in proteins", Genetics, 176:1459-1472 (2005).
Barba, Clara, et al. "Restoring important hair properties with wool keratin pro-teins and peptides." Fibers and Polymers 11.7 (2010): 1055-1061.
Barthelemy, et al., "Proteomic tools for the investigation of human hair structural pro-teins and evidence of weakness sites on hair keratin coil segments" Analytical Biochemistry 421.1 (Feb. 1, 2012): 43-55.
Roddick-Lanzilotta, Alisa, et al. "New keratin isolates: actives for natural hair protection." Journal of cosmetic science 58.4 (2007): 405-411.
Griesbach, et al., "Protection and Care for Hair and Skin—The Latest on the Subject of Proteins" Cossma, English Edition Online 11.11 (Nov. 2010): 28-30.
Bringans, et al., "Characterization of the exocuticle a-layer proteins of wool" Experimental Dermatology 16.11 (Nov. 2007): 951-960.
Koehn, et al., "Higher sequence coverage and improved confidence in the identifi-cation of cysteine-rich proteins from the wool cuticle using com-bined chemical and enzymatic digestion" Journal of Proteomics 73.2 (Dec. 1, 2009): 323-330. Copyright © 2021 ProQuest LLC.
Mukhtarov, et al., "Keratine Enzymatic Hydrolysates for Cosmetics" 6th International Scientific—Practical Confer-Ence "Cosmetic Products and Raw Materials: Efficacy and Safety" 106 C : CC C (2001).

(Continued)

*Primary Examiner* — Sergio Coffa
(74) *Attorney, Agent, or Firm* — PABST PATENT GROUP LLP

(57) ABSTRACT

Peptides are provided herein, wherein the peptide bearing one or more amino acid sequence differences relative to SEQ ID NO: 1, with the amino acid sequence differences comprising at least one cysteine replacement or addition.

25 Claims, 24 Drawing Sheets

Specification includes a Sequence Listing.

(56) References Cited

OTHER PUBLICATIONS

Fernandes, et al., Protein disulphide isomerase-assisted functionalization of keratin-based matrices, Appl. Microbiol. Biotechnol, 90:1311-1321 (2011).

Fernandes, "Protein disulphide isomerase-mediated grafting of cysteine containing peptides onto over-bleached hair," Biocatalysis and Biotransformation, Jan.-Feb. 2012; 30(1): 10-19 [Published online: Dec. 16, 2011].

Fernandes, et al., "Keratin-based peptide: biological evaluation and strengthening properties on relaxed hair," International Journal of Cosmetic Science, 34, 338-346 (2012) (Fernandes 2012b) [Epub May 17, 2012].

Robbins, et al., "Chemical and Physical Behavior of Human Hair" DOI 10.1007/978-3-642-25611-0 (2012).

FIGURE 11(a)

QGQVQHLQAAFSQYKKVELFPK
KKVELFPK
CGQVCHLQCAFSCYKKCELFPK
QGQVCHLQCAFSCYKKCELFPK
QGQCCHLQCCFSQYKKCELFPKC
CGQCCHLQCCFCCYKKCELFPKC
CGCCCHLCCCFCCYKKCELFPKC
CGQVCHLQCAFSCYKKCELFPKC
CQGQVQHLQAAFSQYKKVELFPKC
CQGQVQHLQAAFSQYKKCELFPKC
QGQVQHLQCAFSCYKKCELFPK
QGQVQHLQAAFSCYKKCELFPK
QGQVQHLQAAFSCYKKVELFPK
CGQCCHLQCCFCQYKKCELFPKC
CGCCCHLCCCFCQYKKCELFPKC
CGQVCHLQCAFSQYKKCELFPKC
CGQVCHLQCAFSGYKKCELFPKC
CGQVCHLQCAFSCYKKCELFAK
CGQAQHLCAAFSQYKKVELFPK
CCQCQHCQCCCSCYKKVECFPC
QCQVQCCQACCSQYKCVELFPC
QGQVQHLQAACCQCCCVELFPC
QCQVQHLCCCFCCYKKVECCPC
QAQVQHACAACSAYKKCELFAC
QGCCQHCQCACSQCCKVECCCK
QCQCQCLQAAFCCYCKVELCPK
QGC

FIGURE 11(b)

CCQCCHCQCCFSQYCKVCCFPK
QGQVQHCQAAFSQYKCVCLFPK
CGCCQCLAAACSQYKAVCACPK
QGCVQHLQACCCQYCKVELCPK
QGCVQHLQAACSQYKKVELFPK
QGQVQALQAAFSQCAKVEAFPK
QGQVQHLQACFSQYKKCELFPK
QCCCQHCQAACSQAKACCCPK
QCACACLCCACCCCKAAECFCK
QACVQALAACFSQCKCVCLCPC
CCQVQCCCAACCQYCKVECFPK
QGQVQHCCAAFSQYKKVELFPK
QGCVCHLCCCCCCCKCVECFCK
QCQAQCACAACCQYKKVACFPK
QGQCCCLQCACCQYCKCECFPC
CGQVCCCQACFSCCCKCCLFCK
QGCVACLQCAFSQYKKCAACPC
CGCVQHCQAAFCQYAKVCLFAK
QGCCCHCCCCFCQCCCVELFPC
QGQCQHCQAAFSQACKAELFPK
CCCVCCCQAACSAYCCCCACPK
CGCVQHLQACFSQCCCVELCCC
QCQAQHLQACASQYKKVALFPK
QGCCQHLCAAFSQYKCVELFPK
CGQVQHLCAAFSQYCKVEAFPC
QGACQCCCAAASQYACVELFPK
CGQVCHLQACFAQYKCVELFPK
CGCCAALCACCSCYKKACCFPA
QGQVQHLCACCSCYKKVCCCCC
CCCCQAACCACSCYCKVELFCK
QCQVQHLQAAFCQCKCCELCPK

FIGURE 11 (c)

QGQVQCLCAAFSQYKKCECFPK
CGCACALAACCSCCCCVALFPK
QAQAQHLCCAFCCCKKCELCPK
CGCCQHLQCCFCCYKCVCCFPK
CCQCQCLCAAFSCYKKVCCCPK
QACAQCLCAAFSQYAKVELFPK
QGQVQHLQCAFCCYKKVELFPK
QGQVQHLQACFSCYKCVELFPC
QGQVCCCAAFCCCKCVELCCK
QGQVQHCQAAFSQYCKVELAAK
QGQVQHLQAAFSQYKKVCLFPK
QGQVQCLQAAFCQCKKVECFPK
QGCVQCLQCACCACKCCCLFCA
CACCQACCACFSCAKCAECFCK
QGQVQHCQAAFSQYKKCCLFPK
QAQVQHLQAAFSQCCCVELFCK
CCQCCCLCCAFCCCCKCELFPK
QGQVQCLCCCCSQYKKVECFPK
QGQVQHLQACFSAYKKVELFPK
QGQVCHCCCAFAQYKCACAFPK
QGQCQCLCAAFCCYKKVELCPK
QGQVQCLQAAASQYKKCELFCK
QGQVQCCQAACSQYKKVELFPC
AGCVQCLCCCCCCYAKVCAFPK
QGCCQCCCACCSQYKKVELFPC
ACQVQHCCCAFCCYCCVCCFCC
CCCCQHLCACFSCYCKVECFCK
QGQVQHLQCAFSCYKKVELFCC
CGQVQHLQAACSQYKCVELFCK
QCCVCCAQACFCQYKKCECCCA
CGAVQCCCACFCCCAKVECFCA

FIGURE 11(d)

CGCCQCLCAACSCYCCVCLCCK
QGQVQCLQCAFSQAKCAEAFPA
QGCAQHACAAFSQYKAVELFPC
QGCVQHLQCACSQYKKCELACK
QGQCCHLQAAFSQYKKAELFPK
CCCCAHCACAFSQYKCACCCPC
CCQCQHLAACFAQYCACCCCCK
CCCVCCLQAACCCYKKCCLCCK
AGCCQCCCCAFCQYKKCCCFCC
QGQVQCLQCAFCCYKKVELFCC
CCQVCHLQCCAACYKKCCLFPC
CCQCQHAQCAFCACCCCACCCK
QGQVQHLQAAFSQCCACECFPK
QGACQALQAAFCQYKKVCAFCK
QCCCQHCQACCCCYKKCCCCPK
QGCVCHLQAACSQYKKV

SEQUENCE LISTING

```
Sequence total quantity: 109
SEQ ID NO: 1            moltype = AA  length = 22
FEATURE                 Location/Qualifiers
REGION                  1..22
                        note = Peptide
source                  1..22
                        mol_type = protein
                        organism = synthetic construct
SEQUENCE: 1
QGQVQHLQAA FSQYKKVELF PK                                                 22

SEQ ID NO: 2            moltype = AA  length = 8
FEATURE                 Location/Qualifiers
REGION                  1..8
                        note = peptide
source                  1..8
                        mol_type = protein
                        organism = synthetic construct
SEQUENCE: 2
KKVELFPK                                                                 8

SEQ ID NO: 3            moltype = AA  length = 22
FEATURE                 Location/Qualifiers
REGION                  1..22
                        note = peptide
source                  1..22
                        mol_type = protein
                        organism = synthetic construct
SEQUENCE: 3
CGQVCHLQCA FSCYKKCELF PK                                                 22

SEQ ID NO: 4            moltype = AA  length = 22
FEATURE                 Location/Qualifiers
REGION                  1..22
                        note = peptide
source                  1..22
                        mol_type = protein
                        organism = synthetic construct
SEQUENCE: 4
QGQVCHLQCA FSCYKKCELF PK                                                 22

SEQ ID NO: 5            moltype = AA  length = 23
FEATURE                 Location/Qualifiers
REGION                  1..23
                        note = peptide
source                  1..23
                        mol_type = protein
```

```
                    organism = synthetic construct
SEQUENCE: 5
QGQCCHLQCC FSQYKKCELF PKC                                         23

SEQ ID NO: 6            moltype = AA  length = 23
FEATURE                 Location/Qualifiers
REGION                  1..23
                        note = peptide
source                  1..23
                        mol_type = protein
                        organism = synthetic construct
SEQUENCE: 6
CGQCCHLQCC FCCYKKCELF PKC                                         23

SEQ ID NO: 7            moltype = AA  length = 23
FEATURE                 Location/Qualifiers
REGION                  1..23
                        note = peptide
source                  1..23
                        mol_type = protein
                        organism = synthetic construct
SEQUENCE: 7
CGCCCHLCCC FCCYKKCELF PKC                                         23

SEQ ID NO: 8            moltype = AA  length = 23
FEATURE                 Location/Qualifiers
REGION                  1..23
                        note = peptide
source                  1..23
                        mol_type = protein
                        organism = synthetic construct
SEQUENCE: 8
CGQVCHLQCA FSCYKKCELF PKC                                         23

SEQ ID NO: 9            moltype = AA  length = 24
FEATURE                 Location/Qualifiers
REGION                  1..24
                        note = peptide
source                  1..24
                        mol_type = protein
                        organism = synthetic construct
SEQUENCE: 9
CQGQVQHLQA AFSQYKKVEL FPKC                                        24

SEQ ID NO: 10           moltype = AA  length = 24
FEATURE                 Location/Qualifiers
REGION                  1..24
                        note = peptide
source                  1..24
                        mol_type = protein
                        organism = synthetic construct
SEQUENCE: 10
CQGQVQHLQA AFSQYKKCEL FPKC                                        24

SEQ ID NO: 11           moltype = AA  length = 22
FEATURE                 Location/Qualifiers
REGION                  1..22
                        note = peptide
source                  1..22
                        mol_type = protein
                        organism = synthetic construct
SEQUENCE: 11
QGVVQHLQCA FSCYKKCELF PK                                          22

SEQ ID NO: 12           moltype = AA  length = 22
FEATURE                 Location/Qualifiers
REGION                  1..22
                        note = peptide
source                  1..22
                        mol_type = protein
                        organism = synthetic construct
SEQUENCE: 12
QGVVQHLQAA FSCYKKCELF PK                                          22

SEQ ID NO: 13           moltype = AA  length = 22
FEATURE                 Location/Qualifiers
REGION                  1..22
                        note = peptide
source                  1..22
```

```
                            mol_type = protein
                            organism = synthetic construct
SEQUENCE: 13
QGQVQHLQAA FSCYKKVELF PK                                                    22

SEQ ID NO: 14               moltype = AA   length = 23
FEATURE                     Location/Qualifiers
REGION                      1..23
                            note = peptide
source                      1..23
                            mol_type = protein
                            organism = synthetic construct
SEQUENCE: 14
CGQCCHLQCC FCQYKKCELF PKC                                                   23

SEQ ID NO: 15               moltype = AA   length = 23
FEATURE                     Location/Qualifiers
REGION                      1..23
                            note = peptide
source                      1..23
                            mol_type = protein
                            organism = synthetic construct
SEQUENCE: 15
CGCCCHLCCC FCQYKKCELF PKC                                                   23

SEQ ID NO: 16               moltype = AA   length = 23
FEATURE                     Location/Qualifiers
REGION                      1..23
                            note = peptide
source                      1..23
                            mol_type = protein
                            organism = synthetic construct
SEQUENCE: 16
CGQVCHLQCA FSQYKKCELF PKC                                                   23

SEQ ID NO: 17               moltype = AA   length = 23
FEATURE                     Location/Qualifiers
REGION                      1..23
                            note = peptide
source                      1..23
                            mol_type = protein
                            organism = synthetic construct
SEQUENCE: 17
CGQVCHLQCA FSGYKKCELF PKC                                                   23

SEQ ID NO: 18               moltype = AA   length = 22
FEATURE                     Location/Qualifiers
REGION                      1..22
                            note = peptide
source                      1..22
                            mol_type = protein
                            organism = synthetic construct
SEQUENCE: 18
CGQVCHLQCA FSCYKKCELF AK                                                    22

SEQ ID NO: 19               moltype = AA   length = 22
FEATURE                     Location/Qualifiers
REGION                      1..22
                            note = peptide
source                      1..22
                            mol_type = protein
                            organism = synthetic construct
SEQUENCE: 19
CGQAQHLCAA FSQYKKVELF PK                                                    22

SEQ ID NO: 20               moltype = AA   length = 22
FEATURE                     Location/Qualifiers
REGION                      1..22
                            note = peptide
source                      1..22
                            mol_type = protein
                            organism = synthetic construct
SEQUENCE: 20
CCQCQHCQCC CSCYKKVECF PC                                                    22

SEQ ID NO: 21               moltype = AA   length = 22
FEATURE                     Location/Qualifiers
REGION                      1..22
                            note = peptide
```

```
source                          1..22
                                mol_type = protein
                                organism = synthetic construct
SEQUENCE: 21
QCQVQCCQAC CSQYKCVELF PC                                                  22

SEQ ID NO: 22                   moltype = AA   length = 22
FEATURE                         Location/Qualifiers
REGION                          1..22
                                note = peptide
source                          1..22
                                mol_type = protein
                                organism = synthetic construct
SEQUENCE: 22
QGQVQHLQAA CCQCCCVELF PC                                                  22

SEQ ID NO: 23                   moltype = AA   length = 22
FEATURE                         Location/Qualifiers
REGION                          1..22
                                note = peptide
source                          1..22
                                mol_type = protein
                                organism = synthetic construct
SEQUENCE: 23
QCQVQHLCCC FCCYKKVECC PC                                                  22

SEQ ID NO: 24                   moltype = AA   length = 22
FEATURE                         Location/Qualifiers
REGION                          1..22
                                note = peptide
source                          1..22
                                mol_type = protein
                                organism = synthetic construct
SEQUENCE: 24
QAQVQHACAA CSAYKKCELF AC                                                  22

SEQ ID NO: 25                   moltype = AA   length = 22
FEATURE                         Location/Qualifiers
REGION                          1..22
                                note = peptide
source                          1..22
                                mol_type = protein
                                organism = synthetic construct
SEQUENCE: 25
QGCCQHCQCA CSQCCKVECC CK                                                  22

SEQ ID NO: 26                   moltype = AA   length = 22
FEATURE                         Location/Qualifiers
REGION                          1..22
                                note = peptide
source                          1..22
                                mol_type = protein
                                organism = synthetic construct
SEQUENCE: 26
QCQCQCLQAA FCCYCKVELC PK                                                  22

SEQ ID NO: 27                   moltype = AA   length = 22
FEATURE                         Location/Qualifiers
REGION                          1..22
                                note = peptide
source                          1..22
                                mol_type = protein
                                organism = synthetic construct
SEQUENCE: 27
QGCCCHCQCA FCQYCACELC PK                                                  22

SEQ ID NO: 28                   moltype = AA   length = 22
FEATURE                         Location/Qualifiers
REGION                          1..22
                                note = peptide
source                          1..22
                                mol_type = protein
                                organism = synthetic construct
SEQUENCE: 28
QGCVCHLQAA CSQYKKCELF PC                                                  22

SEQ ID NO: 29                   moltype = AA   length = 22
FEATURE                         Location/Qualifiers
REGION                          1..22
```

```
                        note = peptide
source                  1..22
                        mol_type = protein
                        organism = synthetic construct
SEQUENCE: 29
QGVQHLQAA CSQYKCAECF PK                                          22

SEQ ID NO: 30           moltype = AA  length = 22
FEATURE                 Location/Qualifiers
REGION                  1..22
                        note = peptide
source                  1..22
                        mol_type = protein
                        organism = synthetic construct
SEQUENCE: 30
QACVQHCQCC FCQAKAVELC PK                                         22

SEQ ID NO: 31           moltype = AA  length = 22
FEATURE                 Location/Qualifiers
REGION                  1..22
                        note = peptide
source                  1..22
                        mol_type = protein
                        organism = synthetic construct
SEQUENCE: 31
QGCCQCCQAA CACCCACECF PC                                         22

SEQ ID NO: 32           moltype = AA  length = 22
FEATURE                 Location/Qualifiers
REGION                  1..22
                        note = peptide
source                  1..22
                        mol_type = protein
                        organism = synthetic construct
SEQUENCE: 32
CCQCCHCQCC FSQYCKVCCF PK                                         22

SEQ ID NO: 33           moltype = AA  length = 22
FEATURE                 Location/Qualifiers
REGION                  1..22
                        note = peptide
source                  1..22
                        mol_type = protein
                        organism = synthetic construct
SEQUENCE: 33
QGVQHCQAA FSQYKCVCLF PK                                          22

SEQ ID NO: 34           moltype = AA  length = 22
FEATURE                 Location/Qualifiers
REGION                  1..22
                        note = peptide
source                  1..22
                        mol_type = protein
                        organism = synthetic construct
SEQUENCE: 34
CGCCQCLAAA CSQYKAVCAC PK                                         22

SEQ ID NO: 35           moltype = AA  length = 22
FEATURE                 Location/Qualifiers
REGION                  1..22
                        note = peptide
source                  1..22
                        mol_type = protein
                        organism = synthetic construct
SEQUENCE: 35
QGCVQHLQAC CCQYCKVELC PK                                         22

SEQ ID NO: 36           moltype = AA  length = 22
FEATURE                 Location/Qualifiers
REGION                  1..22
                        note = peptide
source                  1..22
                        mol_type = protein
                        organism = synthetic construct
SEQUENCE: 36
QGCVQHLQAA CSQYKKVELF PK                                         22

SEQ ID NO: 37           moltype = AA  length = 22
FEATURE                 Location/Qualifiers
```

```
REGION                      1..22
                            note = peptide
source                      1..22
                            mol_type = protein
                            organism = synthetic construct
SEQUENCE: 37
QGQVQALQAA FSQCAKVEAF PK                                                    22

SEQ ID NO: 38               moltype = AA  length = 22
FEATURE                     Location/Qualifiers
REGION                      1..22
                            note = peptide
source                      1..22
                            mol_type = protein
                            organism = synthetic construct
SEQUENCE: 38
QGQVQHLQAC FSQYKKCELF PK                                                    22

SEQ ID NO: 39               moltype = AA  length = 22
FEATURE                     Location/Qualifiers
REGION                      1..22
                            note = peptide
source                      1..22
                            mol_type = protein
                            organism = synthetic construct
SEQUENCE: 39
QCCCQHCQAA CSQAKACCCC PK                                                    22

SEQ ID NO: 40               moltype = AA  length = 22
FEATURE                     Location/Qualifiers
REGION                      1..22
                            note = peptide
source                      1..22
                            mol_type = protein
                            organism = synthetic construct
SEQUENCE: 40
QCACACLCCA CCCCKAAECF CK                                                    22

SEQ ID NO: 41               moltype = AA  length = 22
FEATURE                     Location/Qualifiers
REGION                      1..22
                            note = peptide
source                      1..22
                            mol_type = protein
                            organism = synthetic construct
SEQUENCE: 41
QACVQALAAC FSQCKCVCLC PC                                                    22

SEQ ID NO: 42               moltype = AA  length = 22
FEATURE                     Location/Qualifiers
REGION                      1..22
                            note = peptide
source                      1..22
                            mol_type = protein
                            organism = synthetic construct
SEQUENCE: 42
CCQVQCCCAA CCQYCKVECF PK                                                    22

SEQ ID NO: 43               moltype = AA  length = 22
FEATURE                     Location/Qualifiers
REGION                      1..22
                            note = peptide
source                      1..22
                            mol_type = protein
                            organism = synthetic construct
SEQUENCE: 43
QGQVQHCCAA FSQYKKVELF PK                                                    22

SEQ ID NO: 44               moltype = AA  length = 22
FEATURE                     Location/Qualifiers
REGION                      1..22
                            note = peptide
source                      1..22
                            mol_type = protein
                            organism = synthetic construct
SEQUENCE: 44
QGCVCHLCCC CCCCKCVECF CK                                                    22

SEQ ID NO: 45               moltype = AA  length = 22
```

```
                        -continued

FEATURE                 Location/Qualifiers
REGION                  1..22
                        note = peptide
source                  1..22
                        mol_type = protein
                        organism = synthetic construct
SEQUENCE: 45
QCQAQCACAA CCQYKKVACF PK                                          22

SEQ ID NO: 46           moltype = AA  length = 22
FEATURE                 Location/Qualifiers
REGION                  1..22
                        note = peptide
source                  1..22
                        mol_type = protein
                        organism = synthetic construct
SEQUENCE: 46
QGQCCCLQCA CCQYCKCECF PC                                          22

SEQ ID NO: 47           moltype = AA  length = 22
FEATURE                 Location/Qualifiers
REGION                  1..22
                        note = peptide
source                  1..22
                        mol_type = protein
                        organism = synthetic construct
SEQUENCE: 47
CGQVCCCQAC FSCCCKCCLF CK                                          22

SEQ ID NO: 48           moltype = AA  length = 22
FEATURE                 Location/Qualifiers
REGION                  1..22
                        note = peptide
source                  1..22
                        mol_type = protein
                        organism = synthetic construct
SEQUENCE: 48
QGCVACLQCA FSQYKKCAAC PC                                          22

SEQ ID NO: 49           moltype = AA  length = 22
FEATURE                 Location/Qualifiers
REGION                  1..22
                        note = peptide
source                  1..22
                        mol_type = protein
                        organism = synthetic construct
SEQUENCE: 49
CGCVQHCQAA FCQYAKVCLF AK                                          22

SEQ ID NO: 50           moltype = AA  length = 22
FEATURE                 Location/Qualifiers
REGION                  1..22
                        note = peptide
source                  1..22
                        mol_type = protein
                        organism = synthetic construct
SEQUENCE: 50
QGCCCHCCCC FCQCCCVELF PC                                          22

SEQ ID NO: 51           moltype = AA  length = 22
FEATURE                 Location/Qualifiers
REGION                  1..22
                        note = peptide
source                  1..22
                        mol_type = protein
                        organism = synthetic construct
SEQUENCE: 51
QGQCQHCQAA FSQACKAELF PK                                          22

SEQ ID NO: 52           moltype = AA  length = 22
FEATURE                 Location/Qualifiers
REGION                  1..22
                        note = peptide
source                  1..22
                        mol_type = protein
                        organism = synthetic construct
SEQUENCE: 52
CCCVCCCQAA CSAYCCCCAC PK                                          22
```

```
SEQ ID NO: 53          moltype = AA   length = 22
FEATURE                Location/Qualifiers
REGION                 1..22
                       note = peptide
source                 1..22
                       mol_type = protein
                       organism = synthetic construct
SEQUENCE: 53
CGCVQHLQAC FSQCCCVELC CC                                              22

SEQ ID NO: 54          moltype = AA   length = 22
FEATURE                Location/Qualifiers
REGION                 1..22
                       note = peptide
source                 1..22
                       mol_type = protein
                       organism = synthetic construct
SEQUENCE: 54
QCQAQHLQAC ASQYKKVALF PK                                              22

SEQ ID NO: 55          moltype = AA   length = 22
FEATURE                Location/Qualifiers
REGION                 1..22
                       note = peptide
source                 1..22
                       mol_type = protein
                       organism = synthetic construct
SEQUENCE: 55
QGCCQHLCAA FSQYKCVELF PK                                              22

SEQ ID NO: 56          moltype = AA   length = 22
FEATURE                Location/Qualifiers
REGION                 1..22
                       note = peptide
source                 1..22
                       mol_type = protein
                       organism = synthetic construct
SEQUENCE: 56
CGQVQHLCAA FSQYCKVEAF PC                                              22

SEQ ID NO: 57          moltype = AA   length = 22
FEATURE                Location/Qualifiers
REGION                 1..22
                       note = peptide
source                 1..22
                       mol_type = protein
                       organism = synthetic construct
SEQUENCE: 57
QGACQCCCAA ASQYACVELF PK                                              22

SEQ ID NO: 58          moltype = AA   length = 22
FEATURE                Location/Qualifiers
REGION                 1..22
                       note = peptide
source                 1..22
                       mol_type = protein
                       organism = synthetic construct
SEQUENCE: 58
CGQVCHLQAC FAQYKCVELF PK                                              22

SEQ ID NO: 59          moltype = AA   length = 22
FEATURE                Location/Qualifiers
REGION                 1..22
                       note = peptide
source                 1..22
                       mol_type = protein
                       organism = synthetic construct
SEQUENCE: 59
CGCCAALCAC CSCYKKACCF PA                                              22

SEQ ID NO: 60          moltype = AA   length = 22
FEATURE                Location/Qualifiers
REGION                 1..22
                       note = peptide
source                 1..22
                       mol_type = protein
                       organism = synthetic construct
SEQUENCE: 60
QGQVQHLCAC CSCYKKVCCC CC                                              22
```

```
SEQ ID NO: 61            moltype = AA   length = 22
FEATURE                  Location/Qualifiers
REGION                   1..22
                         note = peptide
source                   1..22
                         mol_type = protein
                         organism = synthetic construct
SEQUENCE: 61
CCCCQAACCA CSCYCKVELF CK                                                22

SEQ ID NO: 62            moltype = AA   length = 22
FEATURE                  Location/Qualifiers
REGION                   1..22
                         note = peptide
source                   1..22
                         mol_type = protein
                         organism = synthetic construct
SEQUENCE: 62
QCQVQHLQAA FCQCKCCELC PK                                                22

SEQ ID NO: 63            moltype = AA   length = 22
FEATURE                  Location/Qualifiers
REGION                   1..22
                         note = peptide
source                   1..22
                         mol_type = protein
                         organism = synthetic construct
SEQUENCE: 63
QGQVQCLCAA FSQYKKCECF PK                                                22

SEQ ID NO: 64            moltype = AA   length = 22
FEATURE                  Location/Qualifiers
REGION                   1..22
                         note = peptide
source                   1..22
                         mol_type = protein
                         organism = synthetic construct
SEQUENCE: 64
CGCACALAAC CSCCCCVALF PK                                                22

SEQ ID NO: 65            moltype = AA   length = 22
FEATURE                  Location/Qualifiers
REGION                   1..22
                         note = peptide
source                   1..22
                         mol_type = protein
                         organism = synthetic construct
SEQUENCE: 65
QAQAQHLCCA FCCCKKCELC PK                                                22

SEQ ID NO: 66            moltype = AA   length = 22
FEATURE                  Location/Qualifiers
REGION                   1..22
                         note = peptide
source                   1..22
                         mol_type = protein
                         organism = synthetic construct
SEQUENCE: 66
CGCCQHLQCC FCCYKCVCCF PK                                                22

SEQ ID NO: 67            moltype = AA   length = 22
FEATURE                  Location/Qualifiers
REGION                   1..22
                         note = peptide
source                   1..22
                         mol_type = protein
                         organism = synthetic construct
SEQUENCE: 67
CCQCQCLCAA FSCYKKVCCC PK                                                22

SEQ ID NO: 68            moltype = AA   length = 22
FEATURE                  Location/Qualifiers
REGION                   1..22
                         note = peptide
source                   1..22
                         mol_type = protein
                         organism = synthetic construct
SEQUENCE: 68
```

```
QACAQCLCAA FSQYAKVELF PK                                            22

SEQ ID NO: 69           moltype = AA  length = 22
FEATURE                 Location/Qualifiers
REGION                  1..22
                        note = peptide
source                  1..22
                        mol_type = protein
                        organism = synthetic construct
SEQUENCE: 69
QGQVQHLQCA FCCYKKVELF PK                                            22

SEQ ID NO: 70           moltype = AA  length = 22
FEATURE                 Location/Qualifiers
REGION                  1..22
                        note = peptide
source                  1..22
                        mol_type = protein
                        organism = synthetic construct
SEQUENCE: 70
QGVQHLQAC FSCYKCVELF PC                                             22

SEQ ID NO: 71           moltype = AA  length = 22
FEATURE                 Location/Qualifiers
REGION                  1..22
                        note = peptide
source                  1..22
                        mol_type = protein
                        organism = synthetic construct
SEQUENCE: 71
QGVCCCCAA FCCCKCVELC CK                                             22

SEQ ID NO: 72           moltype = AA  length = 22
FEATURE                 Location/Qualifiers
REGION                  1..22
                        note = peptide
source                  1..22
                        mol_type = protein
                        organism = synthetic construct
SEQUENCE: 72
QGVQHCQAA FSQYCKVELA AK                                             22

SEQ ID NO: 73           moltype = AA  length = 22
FEATURE                 Location/Qualifiers
REGION                  1..22
                        note = peptide
source                  1..22
                        mol_type = protein
                        organism = synthetic construct
SEQUENCE: 73
QGVQHLQAA FSQYKKVCLF PK                                             22

SEQ ID NO: 74           moltype = AA  length = 22
FEATURE                 Location/Qualifiers
REGION                  1..22
                        note = peptide
source                  1..22
                        mol_type = protein
                        organism = synthetic construct
SEQUENCE: 74
QGVQCLQAA FCQCKKVECF PK                                             22

SEQ ID NO: 75           moltype = AA  length = 22
FEATURE                 Location/Qualifiers
REGION                  1..22
                        note = peptide
source                  1..22
                        mol_type = protein
                        organism = synthetic construct
SEQUENCE: 75
QGCVQCLQCA CCACKCCCLF CA                                            22

SEQ ID NO: 76           moltype = AA  length = 22
FEATURE                 Location/Qualifiers
REGION                  1..22
                        note = peptide
source                  1..22
                        mol_type = protein
                        organism = synthetic construct
```

```
SEQUENCE: 76
CACCQACCAC FSCAKCAECF CK                                                22

SEQ ID NO: 77           moltype = AA  length = 22
FEATURE                 Location/Qualifiers
REGION                  1..22
                        note = peptide
source                  1..22
                        mol_type = protein
                        organism = synthetic construct
SEQUENCE: 77
QGQVQHCQAA FSQYKKCCLF PK                                                22

SEQ ID NO: 78           moltype = AA  length = 22
FEATURE                 Location/Qualifiers
REGION                  1..22
                        note = peptide
source                  1..22
                        mol_type = protein
                        organism = synthetic construct
SEQUENCE: 78
QAQVQHLQAA FSQCCCVELF CK                                                22

SEQ ID NO: 79           moltype = AA  length = 22
FEATURE                 Location/Qualifiers
REGION                  1..22
                        note = peptide
source                  1..22
                        mol_type = protein
                        organism = synthetic construct
SEQUENCE: 79
CCQCCCLCCA FCCCCKCELF PK                                                22

SEQ ID NO: 80           moltype = AA  length = 22
FEATURE                 Location/Qualifiers
REGION                  1..22
                        note = peptide
source                  1..22
                        mol_type = protein
                        organism = synthetic construct
SEQUENCE: 80
QGQVQCLCCC CSQYKKVECF PK                                                22

SEQ ID NO: 81           moltype = AA  length = 22
FEATURE                 Location/Qualifiers
REGION                  1..22
                        note = peptide
source                  1..22
                        mol_type = protein
                        organism = synthetic construct
SEQUENCE: 81
QGQVQHLQAC FSAYKKVELF PK                                                22

SEQ ID NO: 82           moltype = AA  length = 22
FEATURE                 Location/Qualifiers
REGION                  1..22
                        note = peptide
source                  1..22
                        mol_type = protein
                        organism = synthetic construct
SEQUENCE: 82
QGQVCHCCCA FAQYKCACAF PK                                                22

SEQ ID NO: 83           moltype = AA  length = 22
FEATURE                 Location/Qualifiers
REGION                  1..22
                        note = peptide
source                  1..22
                        mol_type = protein
                        organism = synthetic construct
SEQUENCE: 83
QGQCQCLCAA FCCYKKVELC PK                                                22

SEQ ID NO: 84           moltype = AA  length = 22
FEATURE                 Location/Qualifiers
REGION                  1..22
                        note = peptide
source                  1..22
                        mol_type = protein
```

```
                                                 -continued
                        organism = synthetic construct
SEQUENCE: 84
QGQVQCLQAA ASQYKKCELF CK                                                    22

SEQ ID NO: 85           moltype = AA  length = 22
FEATURE                 Location/Qualifiers
REGION                  1..22
                        note = peptide
source                  1..22
                        mol_type = protein
                        organism = synthetic construct
SEQUENCE: 85
QGQVQCCQAA CSQYKKVELF PC                                                    22

SEQ ID NO: 86           moltype = AA  length = 22
FEATURE                 Location/Qualifiers
REGION                  1..22
                        note = peptide
source                  1..22
                        mol_type = protein
                        organism = synthetic construct
SEQUENCE: 86
AGCVQCLCCC CCCYAKVCAF PK                                                    22

SEQ ID NO: 87           moltype = AA  length = 22
FEATURE                 Location/Qualifiers
REGION                  1..22
                        note = peptide
source                  1..22
                        mol_type = protein
                        organism = synthetic construct
SEQUENCE: 87
QGCCQCCCAC CSQYKKVELF PC                                                    22

SEQ ID NO: 88           moltype = AA  length = 22
FEATURE                 Location/Qualifiers
REGION                  1..22
                        note = peptide
source                  1..22
                        mol_type = protein
                        organism = synthetic construct
SEQUENCE: 88
ACQVQHCCCA FCCYCCVCCF CC                                                    22

SEQ ID NO: 89           moltype = AA  length = 22
FEATURE                 Location/Qualifiers
REGION                  1..22
                        note = peptide
source                  1..22
                        mol_type = protein
                        organism = synthetic construct
SEQUENCE: 89
CCCCQHLCAC FSCYCKVECF CK                                                    22

SEQ ID NO: 90           moltype = AA  length = 22
FEATURE                 Location/Qualifiers
REGION                  1..22
                        note = peptide
source                  1..22
                        mol_type = protein
                        organism = synthetic construct
SEQUENCE: 90
QGQVQHLQCA FSCYKKVELF CC                                                    22

SEQ ID NO: 91           moltype = AA  length = 22
FEATURE                 Location/Qualifiers
REGION                  1..22
                        note = peptide
source                  1..22
                        mol_type = protein
                        organism = synthetic construct
SEQUENCE: 91
CGQVQHLQAA CSQYKCVELF CK                                                    22

SEQ ID NO: 92           moltype = AA  length = 22
FEATURE                 Location/Qualifiers
REGION                  1..22
                        note = peptide
source                  1..22
```

```
                            mol_type = protein
                            organism = synthetic construct
SEQUENCE: 92
QCCVCCAQAC FCQYKKCECC CA                                              22

SEQ ID NO: 93               moltype = AA  length = 22
FEATURE                     Location/Qualifiers
REGION                      1..22
                            note = peptide
source                      1..22
                            mol_type = protein
                            organism = synthetic construct
SEQUENCE: 93
CGAVQCCCAC FCCCAKVECF CA                                              22

SEQ ID NO: 94               moltype = AA  length = 22
FEATURE                     Location/Qualifiers
REGION                      1..22
                            note = peptide
source                      1..22
                            mol_type = protein
                            organism = synthetic construct
SEQUENCE: 94
CGCCQCLCAA CSCYCCVCLC CK                                              22

SEQ ID NO: 95               moltype = AA  length = 22
FEATURE                     Location/Qualifiers
REGION                      1..22
                            note = peptide
source                      1..22
                            mol_type = protein
                            organism = synthetic construct
SEQUENCE: 95
QGQVQCLQCA FSQAKCAEAF PA                                              22

SEQ ID NO: 96               moltype = AA  length = 22
FEATURE                     Location/Qualifiers
REGION                      1..22
                            note = peptide
source                      1..22
                            mol_type = protein
                            organism = synthetic construct
SEQUENCE: 96
QGCAQHACAA FSQYKAVELF PC                                              22

SEQ ID NO: 97               moltype = AA  length = 22
FEATURE                     Location/Qualifiers
REGION                      1..22
                            note = peptide
source                      1..22
                            mol_type = protein
                            organism = synthetic construct
SEQUENCE: 97
QGCVQHLQCA CSQYKKCELA CK                                              22

SEQ ID NO: 98               moltype = AA  length = 22
FEATURE                     Location/Qualifiers
REGION                      1..22
                            note = peptide
source                      1..22
                            mol_type = protein
                            organism = synthetic construct
SEQUENCE: 98
QGQCCHLQAA FSQYKKAELF PK                                              22

SEQ ID NO: 99               moltype = AA  length = 22
FEATURE                     Location/Qualifiers
REGION                      1..22
                            note = peptide
source                      1..22
                            mol_type = protein
                            organism = synthetic construct
SEQUENCE: 99
CCCCAHCACA FSQYKCACCC PC                                              22

SEQ ID NO: 100              moltype = AA  length = 22
FEATURE                     Location/Qualifiers
REGION                      1..22
                            note = peptide
```

```
source                  1..22
                        mol_type = protein
                        organism = synthetic construct
SEQUENCE: 100
CCQCQHLAAC FAQYCACCCC CK                                        22

SEQ ID NO: 101          moltype = AA   length = 22
FEATURE                 Location/Qualifiers
REGION                  1..22
                        note = peptide
source                  1..22
                        mol_type = protein
                        organism = synthetic construct
SEQUENCE: 101
CCCVCCLQAA CCCYKKCCLC CK                                        22

SEQ ID NO: 102          moltype = AA   length = 22
FEATURE                 Location/Qualifiers
REGION                  1..22
                        note = peptide
source                  1..22
                        mol_type = protein
                        organism = synthetic construct
SEQUENCE: 102
AGCCQCCCCA FCQYKKCCCF CC                                        22

SEQ ID NO: 103          moltype = AA   length = 22
FEATURE                 Location/Qualifiers
REGION                  1..22
                        note = peptide
source                  1..22
                        mol_type = protein
                        organism = synthetic construct
SEQUENCE: 103
QGQVQCLQCA FCCYKKVELF CC                                        22

SEQ ID NO: 104          moltype = AA   length = 22
FEATURE                 Location/Qualifiers
REGION                  1..22
                        note = peptide
source                  1..22
                        mol_type = protein
                        organism = synthetic construct
SEQUENCE: 104
CCQVCHLQCC AACYKKCCLF PC                                        22

SEQ ID NO: 105          moltype = AA   length = 22
FEATURE                 Location/Qualifiers
REGION                  1..22
                        note = peptide
source                  1..22
                        mol_type = protein
                        organism = synthetic construct
SEQUENCE: 105
CCQCQHAQCA FCACCCCACC CK                                        22

SEQ ID NO: 106          moltype = AA   length = 22
FEATURE                 Location/Qualifiers
REGION                  1..22
                        note = peptide
source                  1..22
                        mol_type = protein
                        organism = synthetic construct
SEQUENCE: 106
QGQVQHLQAA FSQCCACECF PK                                        22

SEQ ID NO: 107          moltype = AA   length = 22
FEATURE                 Location/Qualifiers
REGION                  1..22
                        note = peptide
source                  1..22
                        mol_type = protein
                        organism = synthetic construct
SEQUENCE: 107
QGACQALQAA FCQYKKVCAF CK                                        22

SEQ ID NO: 108          moltype = AA   length = 22
FEATURE                 Location/Qualifiers
REGION                  1..22
```

```
                        note = peptide
source                  1..22
                        mol_type = protein
                        organism = synthetic construct
SEQUENCE: 108
QCCCQHCQAC CCCYKKCCCC PK                                            22

SEQ ID NO: 109          moltype = AA  length = 22
FEATURE                 Location/Qualifiers
REGION                  1..22
                        note = peptide
source                  1..22
                        mol_type = protein
                        organism = synthetic construct
SEQUENCE: 109
QGCVCHLQAA CSQYKKVELF PC                                            22
```

COMPOSITIONS AND METHOD OF USE FOR HAIR STRAIGHTENING AND SHAPING

This application claims priority from copending nonprovisional application Ser. No. 17/555,392, which claims priority from provisional application Ser. No. 63/205,666, converted to provisional application Aug. 4, 2021, from nonprovisional application Ser. No. 17/128,036 filed Dec. 19, 2020, the entire disclosures of which is hereby incorporated by reference.

REFERENCE TO SEQUENCE LISTING

The Sequence Listing submitted as a text file named "OLA_200_CON_ST26.xml" created on Nov. 9, 2023, and having a size of 136,819 bytes is hereby incorporated by reference pursuant to 37 C.F.R. § 1.834(c)(1).

BACKGROUND

Keratin refers to the filament-forming proteins presenting specific physiochemical I properties, which can be extracted from the cornified layer of the epidermis. Keratin is the main protein in skin and makes up hair, nails, and the surface layer of the skin. Harsh chemicals and environmental influences such as UV and thermal radiation lead to lasting keratin damage to skin, hair, and nails.

A keratin protein is defined by a primary structure based on amino acid chains. The chains vary in number and sequence of amino acids, polarity, charge, and size. Small modifications in the keratin's amino acid sequence cause significant property modification, since these sequences determine the whole molecular structure and the nature of the bonds. The sulphur-containing amino acids, methionine and cysteine establish intra or intermolecular disulfide bonds. The role of disulphide bonds is important in keratin's structural integrity. The disulfide bonds can be broken by chemical treatment of the hair and over time result in serious long-lasting damage to the keratin.

The keratin intra-strand disulfide bonds result in characteristic waves, curls and the general body or appearance of one's hair. These characteristics of hair can be desirable or undesirable, resulting in an individual seeking hair treatment to change the natural body or shape of their hair. In order to limit or minimize the application of harsh chemicals used to straighten or shape hair into a desired conformation, there is a need to develop safer and more efficient alternative biologically-based compositions. The object of this disclosure is to provide peptides for use in consumer products, cosmetic compositions, hair treatments, and/or hair color.

BRIEF SUMMARY

This disclosure provides information related to a compound that may be used to treat keratin fibers, such as to strengthen and/or reduce or prevent breakage. The objective is attained by providing a cysteine reactive peptide In a first aspect, the peptide has a substitution of at least one amino acid of SEQ ID NO:1 with a cysteine, wherein the peptide comprises at least 50% sequence identity to SEQ ID NO:1. The peptide has at least one cysteine substitution occurs at any one or more of a glutamine amino acid position, a valine amino acid position, an alanine amino acid position, and a serine amino acid position. The peptide forms an alpha helix and at least one of the cysteine substitutions is located on the outside region of the alpha helix.

In an embodiment, the cysteine substitution located in the region of SEQ ID NO:1 identified as SEQ ID NO:2. The cysteine substitution within the SEQ ID NO: 2 can be, for example, a V17C substitution relative to SEQ ID NO:1.

In another embodiment, the peptide has a substitution of an amino acid of SEQ ID NO:1, with a cysteine at H6C or Q13C, and optionally, but preferably an additional cysteine substitution on at least one additional amino acid at another position. The additional cysteine substitution can be from ≥1 to ≤11 amino acids relative to SEQ ID NO: 1.

In another aspect, the peptide has a substitution of at least 3 amino acids of SEQ ID NO: 1, and optionally these cysteine substitutions are on amino acids other than Q13C or H6C positions. In this aspect the cysteine substitutions are ≥3 and ≤11 amino acids relative to SEQ ID NO: 1.

In an embodiment, the cysteine is added at the peptide C-terminus, the N-terminus, or both the N-terminus and C-terminus relative to SEQ ID NO:1.

In a second aspect, the peptide is any one of SEQ ID NOS: 3-108 or a variant thereof with at least 70% sequence identity thereto.

In an embodiment, a composition containing a concentration of a plurality of the peptides disclosed herein increase hair strength relative to a composition containing the same concentration of a plurality of peptides of SEQ ID NO: 1. This can be demonstrated by greater retention in the hair of the peptides disclosed here following repeated washings compared to retention of the same peptides in one washing relative to the same test under the same conditions for the retention of SEQ ID NO:1. The plurality of peptides can be used in a liquid composition to improve one or more properties, for example, hair's strength, visual properties, tactile properties, or a combination thereof. The keratin-bound peptide can be more resistant to washing than a keratin-bound peptide consisting of SEQ ID NO: 1, particularly following damage such as by bleaching one or more time. The liquid composition can be a shampoo, conditioner, oil, or mask. The peptide can be found in a concentration of about 0.01% to about 0.1% w/w of the liquid composition.

In an embodiment, the hair is treated by applying the liquid composition containing the peptide subsequent to application of a hair waving formulation, hair straightening formulation, hair coloring formulation, or hair bleaching formulation to the hair, resulting in a decrease in hair breakage by at least about 5%, 10%, 20%, 30%, 40%, or 50% as compared to when the hair is not treated with the composition following the application of a hair waving formulation, hair straightening formulation, hair coloring formulation, or hair bleaching formulation. As described, the composition can be found as part of a kit.

Definitions

The terms used in this specification generally have their ordinary meanings in the art, within the context of the invention, and in the specific context where each term is used. Certain terms are discussed below, or elsewhere in the specification, to provide additional guidance to the practitioner in describing the compounds, compositions, and methods and how to make and use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. The use of examples anywhere in this specification, including examples of any terms discussed herein, is illustrative only, and in no way limits the scope and meaning of any exemplified term. Likewise, the examples presented are considered non-limiting.

As used herein one embodiment," "an embodiment," "an aspect," "one aspect," indicate inclusion of a particular feature, structure, or characteristic. This is not an inclusion of all possible features, structures, or characteristics. Moreover, such phrases are not necessarily referring to the same aspect or embodiment. Further, when a particular feature, structure, or characteristic is described in connection with an aspect or embodiment, it is submitted that it is within the knowledge of one skilled in the art to affect such feature, structure, or characteristic in connection with other aspects or embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

As used herein, "about" or "approximately" shall generally mean within 20 percent, preferably within 10 percent, and more preferably within 5 percent of a given value or range. Other than in the operating examples, or where otherwise indicated, all numbers expressing quantities of ingredients and/or reaction conditions are to be understood as being modified in all instances by the term "about".

The recitation of numerical ranges by endpoints includes all numbers within that range. By way of non-limiting example, the range "1 to 5" would also include the values 1, 1.5, 2, 2.75, 3, 3.8, 4, 5.

As used in the specification and the appended claims, the singular forms "a", "an", and "the" include plural referents unless the context clearly dictates otherwise.

As used in this specification and the appended claims, the term "or" is generally employed in its sense including "and/or" unless the context clearly indicates otherwise.

As used herein, "hair keratin disulfide" refers to thiol residues naturally existing in hair keratin that form disulfide bonds. The formation of new disulfide bonds between thiol residues and peptides can result in straightened hair, shaped hair, or hair with a desired flow and body.

As used herein "bonding efficiency" refers to the ability to form a chemical bond, such as between the sulfur atoms in two cysteine residues.

As used herein "replacement" refers to the substitution of one amino acid in a protein sequence with another.

As used herein "addition" refers to the insertion of an amino acid between two other amino acids in a protein sequence.

As used herein "residue" refers to an amino acid.

As used herein "bioconjugation site" refers to a chemically reactive moiety that allows attachment to another molecule.

As used herein a "vector" refers to a DNA molecule that allows transcription of the encoded genetic information.

DESCRIPTION OF THE DRAWINGS

FIG. 6(b): Results of Example 6, Break force comparison of hair samples (2) and (3) from FIG. 6a.

FIGS. 11(a)-(d): Sequences tested and described in FIGS. 1-10.

DETAILED DESCRIPTION

Figure 1:
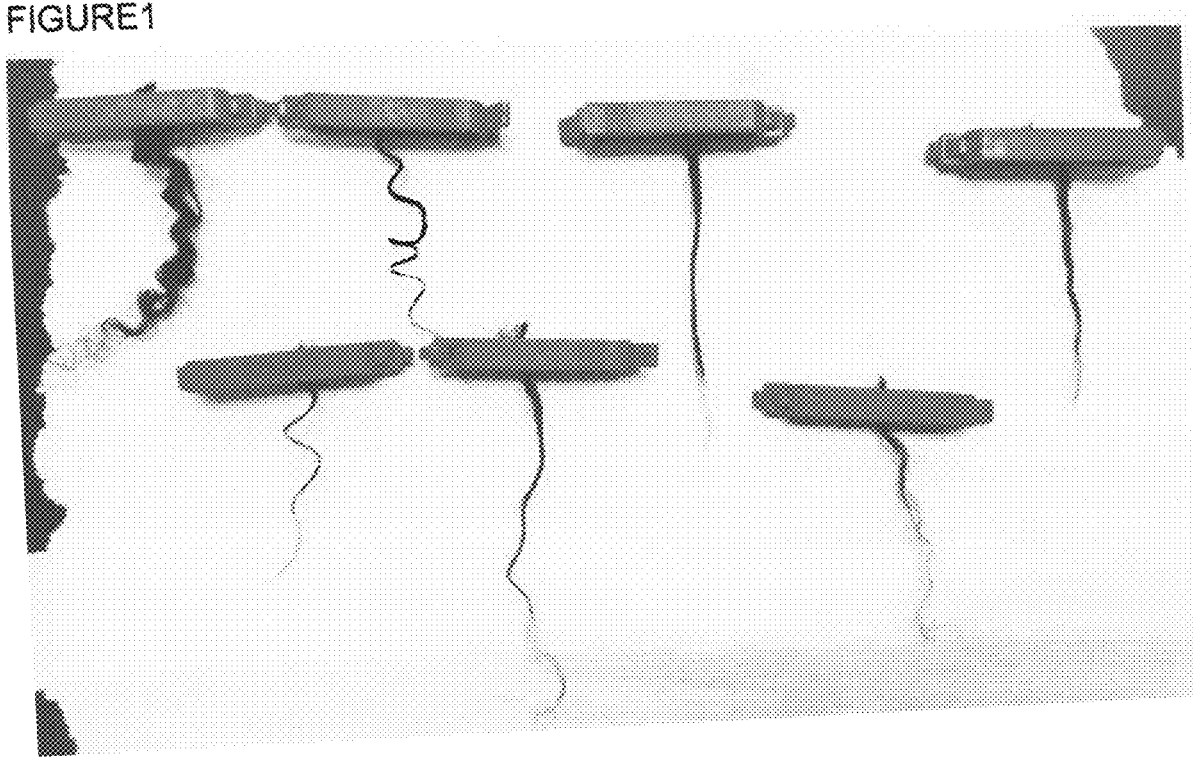
FIG. 1: Results of Example 1, from left to right, hair was treated with: (1) untreated, (2) SEQ ID NO. 3, (3) SEQ ID NO. 4, (4) SEQ ID NO. 5, (5) SEQ ID NO. 6, (6) SEQ ID NO. 7, (7) SEQ ID NO. 8.
Figure 2:
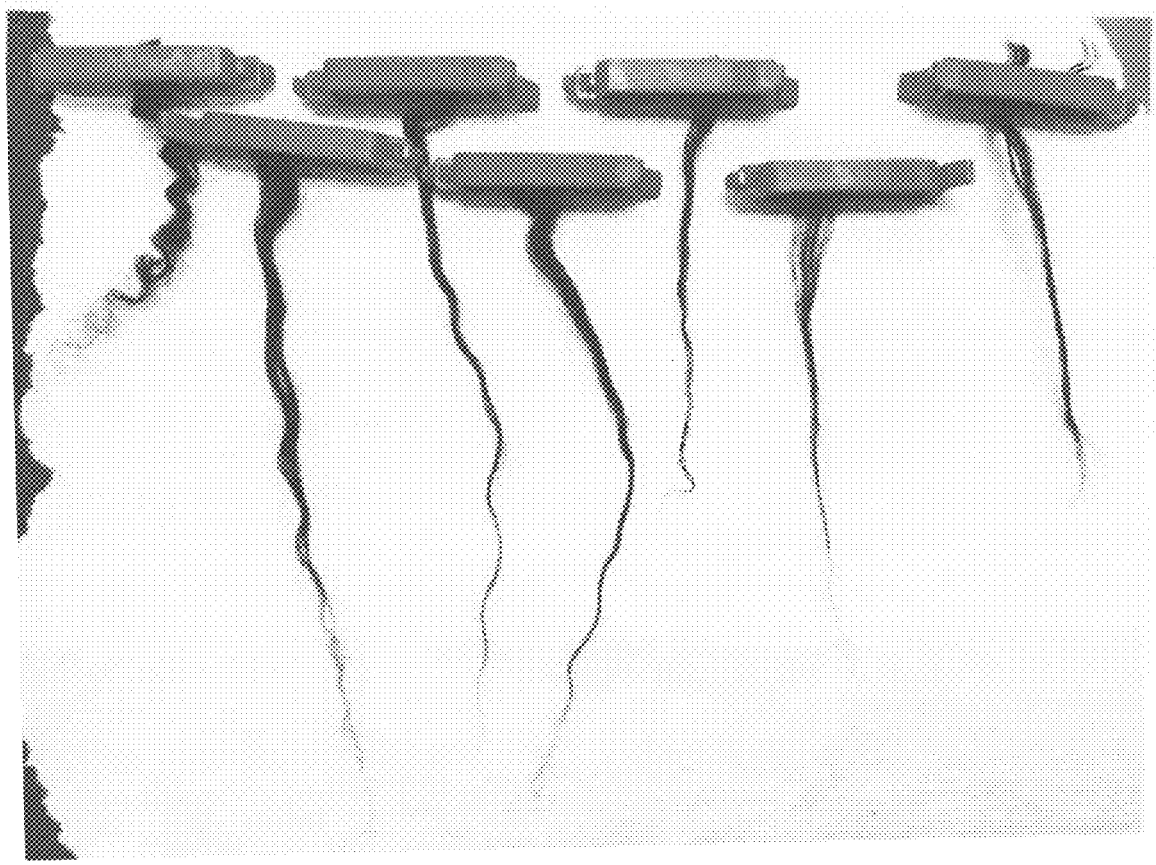
FIG. 2: Results of Example 2, from left to right, hair was treated with: (1) untreated, (2) SEQ ID NO. 3, (3) SEQ ID NO. 4, (4) SEQ ID NO. 5, (5) SEQ ID NO. 6, (6) SEQ ID NO. 7, (7) SEQ ID NO. 8.
Figure 3:
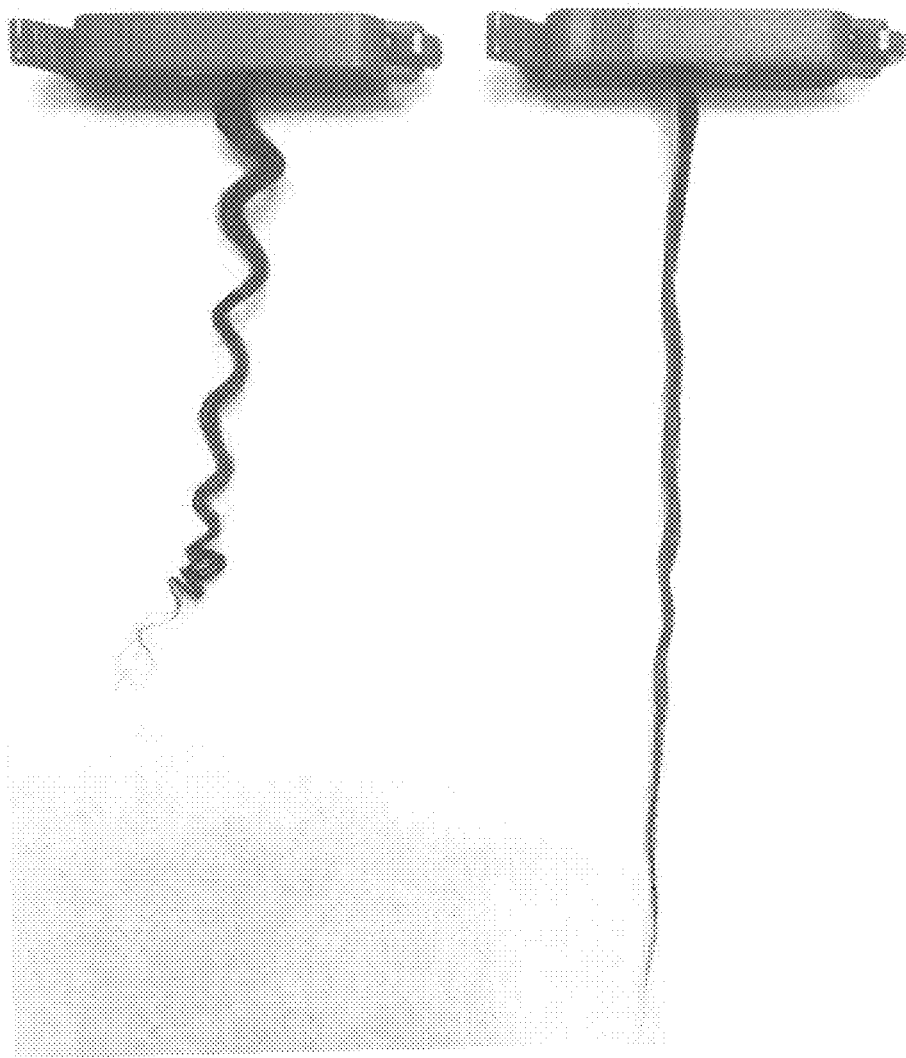
FIG. 3: Results of Example 3, Hair was untreated (left) or treated using the full procedure described in Example 3 (right).
Figure 4:
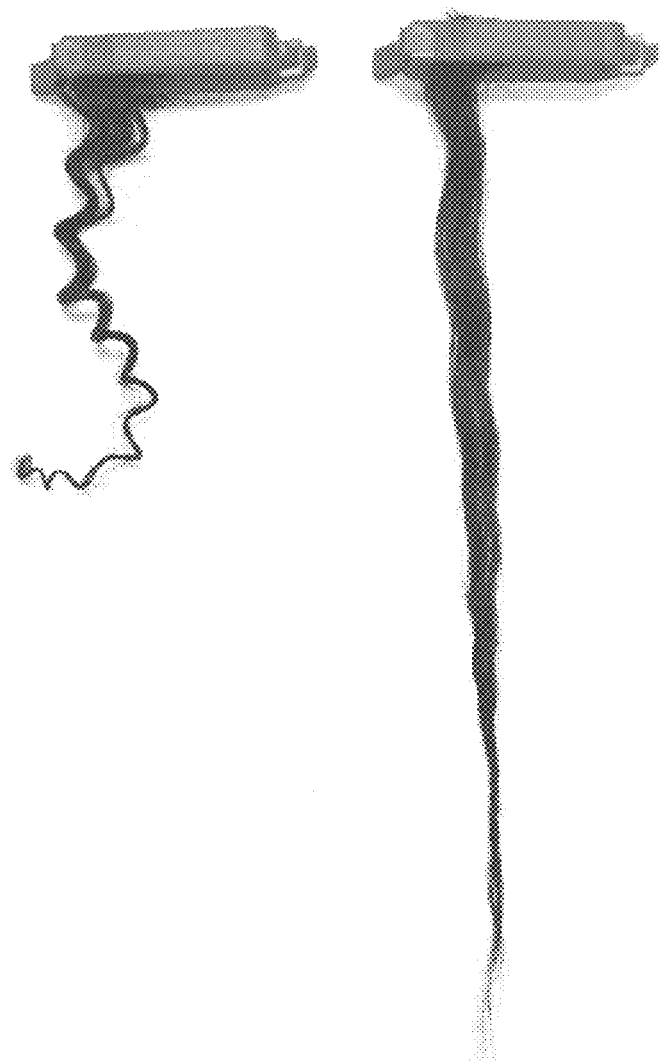
FIG. 4: Results of Example 4, Hair was untreated (left) or treated using the full procedure described in Example 4 (right).
Figure 5:
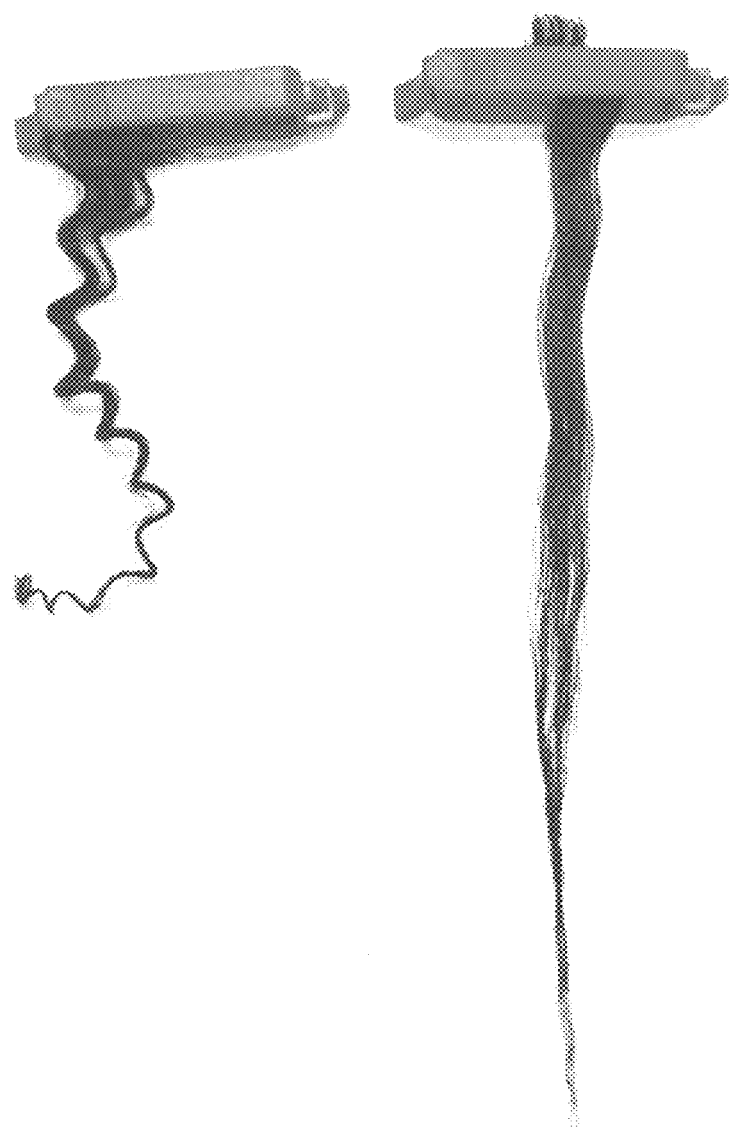
FIG. 5: Results of Example 5, Hair was untreated (left) or treated using the full procedure described in Example 5 (right).
Figure 6A:
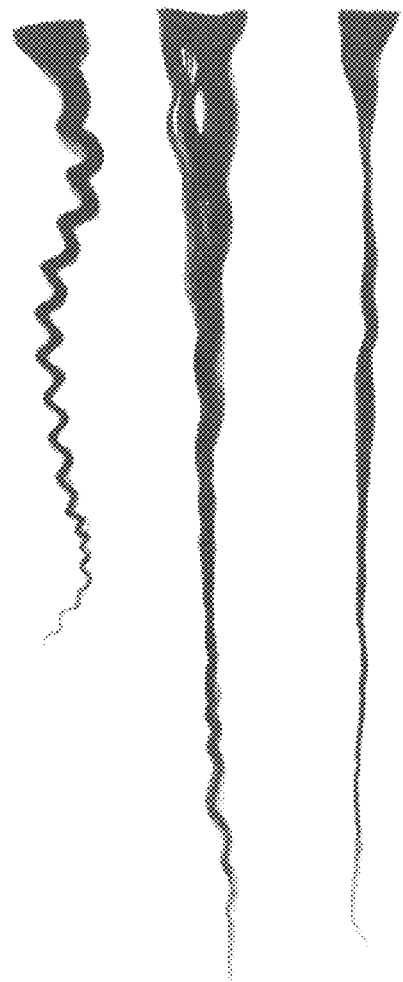
FIG. 6(a): Results of Example 6, From left to right, hair was treated with: (1) untreated, (2) full treatment without SEQ ID NO. 7, (3) full treatment with SEQ ID NO. 7.
Figure 6B:
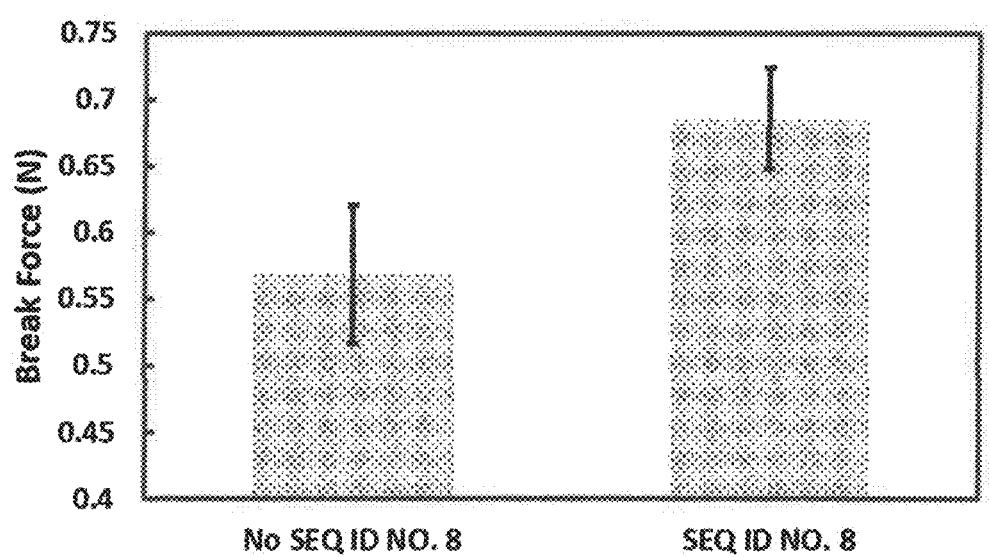
Figure 7A:
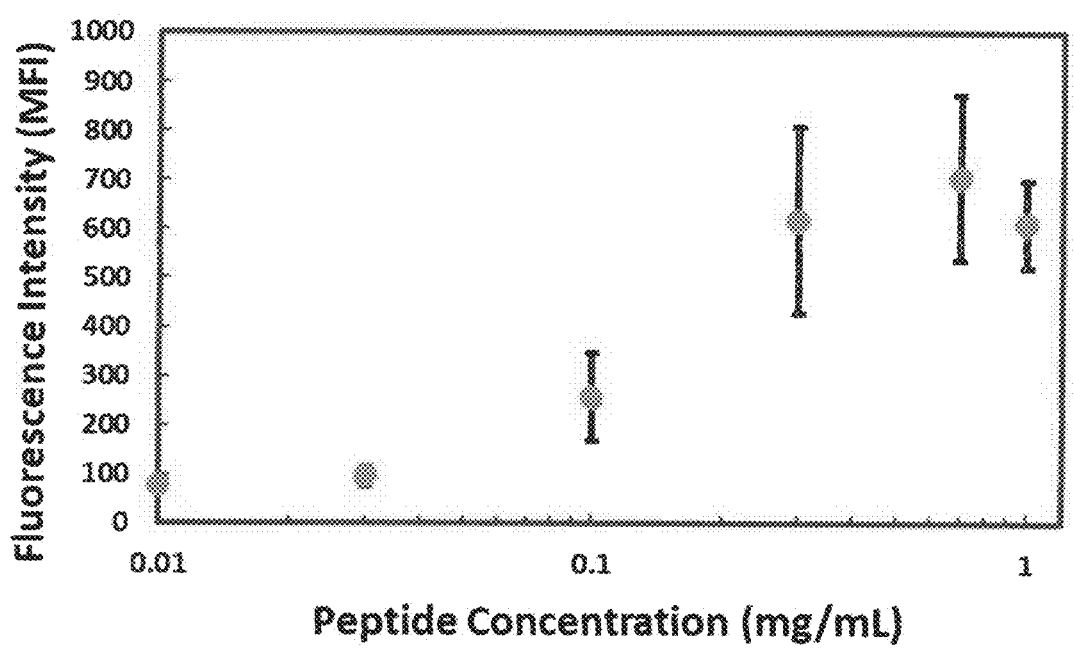
FIG. 7(a): Results of Example 7, demonstrating the effect of varying the peptide concentration.
Figure 7B:
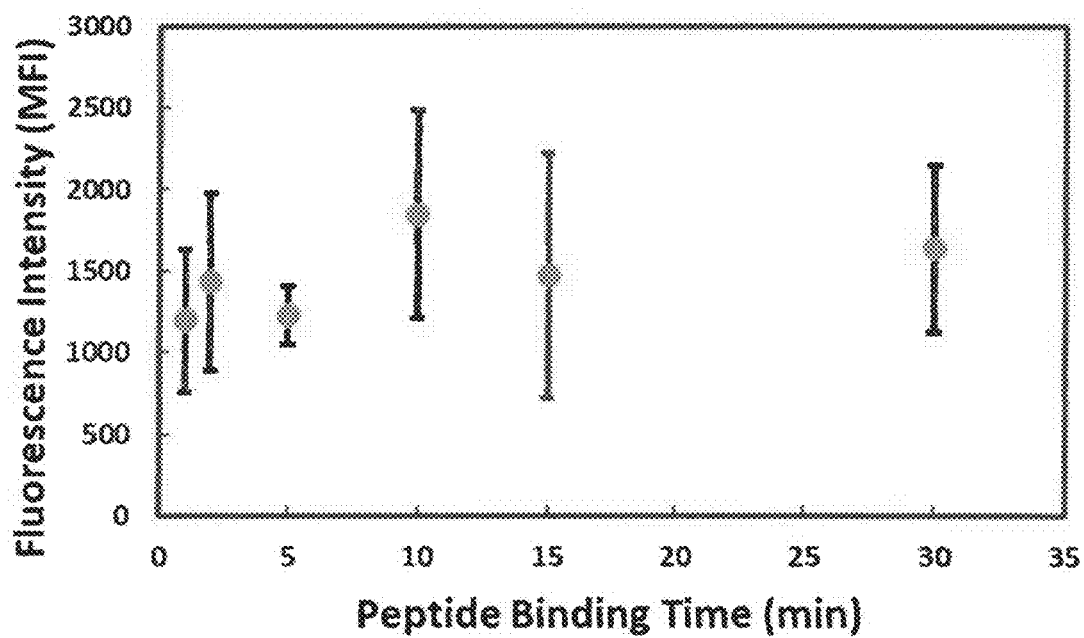
FIG. 7(b): Results of Example 7, demonstrating the effect of varying the peptide binding time.
Figure 7:
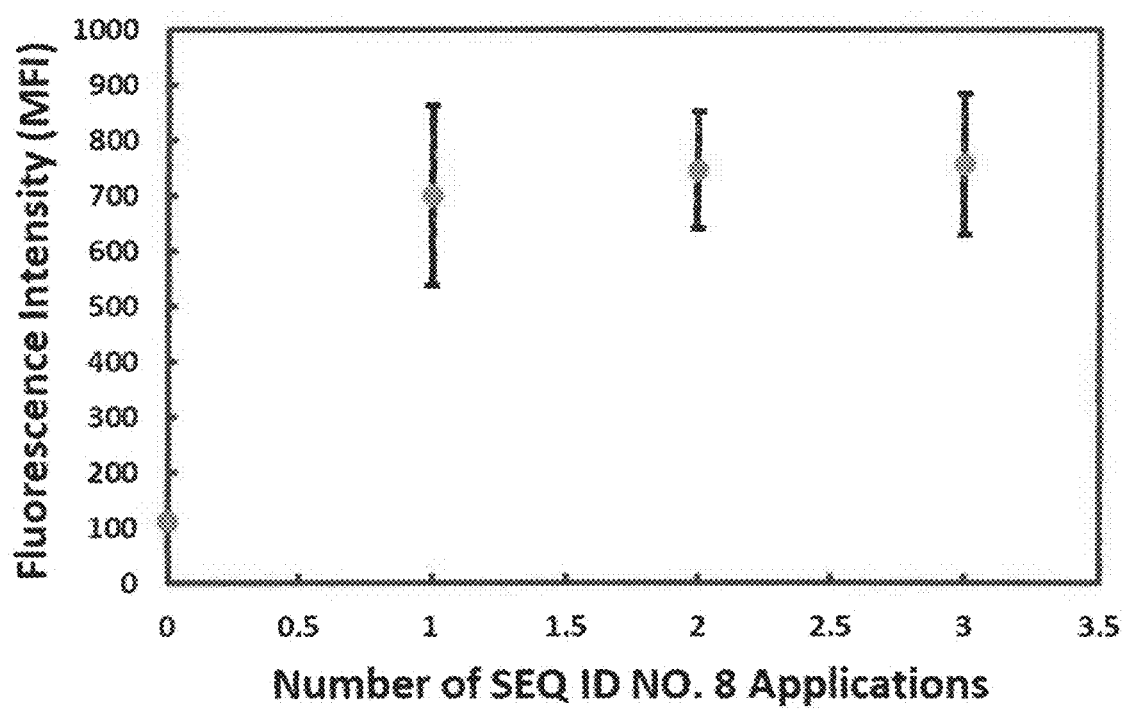
FIG. 7(c): Results of Example 7, demonstrating the effect of varying the number of peptide applications.
FIG. 7(d): Results of Example 7, demonstrating the effect of varying the number of shampoos at the end of treatment.
Figure 7D:
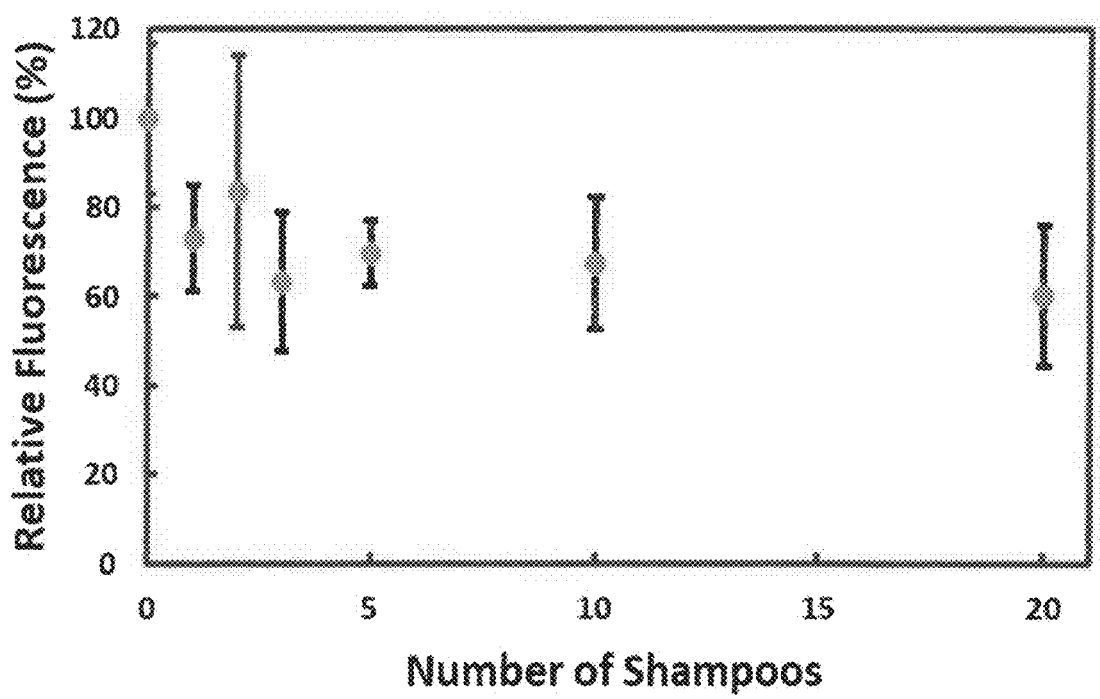
Figure 8A:
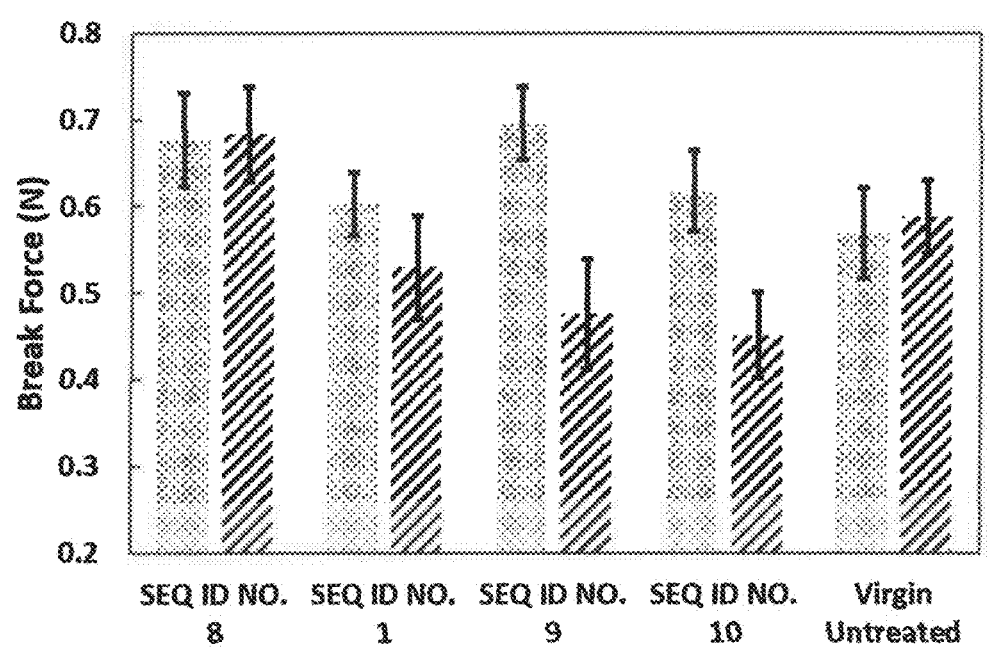
FIG. 8(a): Results of Example 8, demonstrating the break force comparison of treated and untreated virgin hair with different peptides. Dotted bars represent the results after 1 shampoo, and bars with diagonal lines represent the results after 10 shampoos.
Figure 8B:
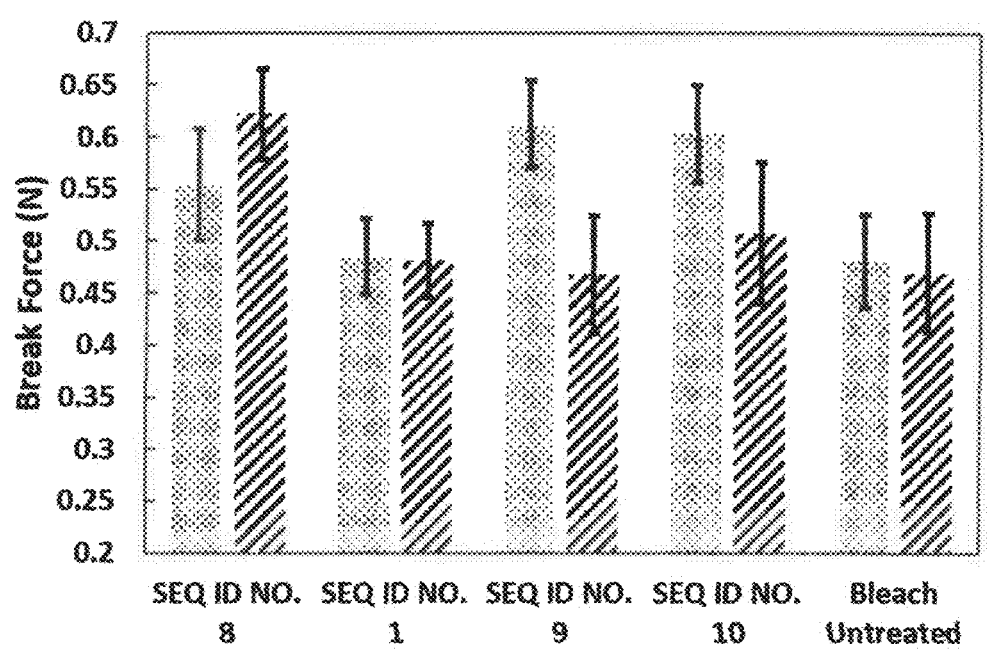
FIG. 8(b): Results of Example 8, demonstrating the break force comparison of treated and untreated bleached virgin hair with different peptides. Dotted bars represent the results after 1 shampoo, and bars with diagonal lines represent the results after 10 shampoos.

While the concepts of the present disclosure are susceptible to various modifications and alternative forms, specific aspects and embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims. It will be apparent to one skilled in the art that various changes or equivalents may be made without departing from the scope herein.

Provided herein are peptides and combinations of such peptides. Such peptides and compositions containing peptides can typically bind to one or more thiol residues naturally existing in hair keratin, thereby allowing for the formation of new disulfide bonds between hair keratin and the designed keratin-binding peptides. Provided herein, for example, is a method to provide a long-lasting shape flow and body to hair accomplished by: 1. mechanically structuring hair keratin into a desired shape (i.e., permanent wave) or into a straightened formation; 2. breaking the hair keratin natural disulfide bonds; and 3. applying the peptides to the hair keratin forming new disulfide bonds between the hair keratin and peptides. In some other instances, methods of treating hair involve applying the peptides to hair prior to and/or following a coloring or bleaching treatment, where the keratin in the treated hair forms new disulfide bonds between the hair keratin and peptides applied. In some instances, methods of treating hair can involve applying the peptides to hair, such as for strengthening hair and/or reducing or preventing breakage in hair, where the peptides can form part of a cosmetic composition, such as in the form of a shampoo, conditioner, oil, or mask, etc. The application of peptides to hair can produce new disulfide bonds between the hair keratin and peptides, which may be part of a cosmetic composition, and are believed to improve one or more properties of the hair, such as but not limited to, increasing hair strength, resistance to breakage, tactile feel (i.e., softness), visual properties (i.e., sheen), as compared to hair prior to treatment with the peptides.

Hair can sustain damage from environmental factors like aging, washing, coloring and styling. Repeated washing results in lifted cuticles, while heat damage from drying, and chemical damage from coloring, bleaching, straightening, or curling hair often leads to dehydrated, easily broken, damaged and frizzy hair. Hair frizz, whether naturally present in the subject's hair or the result of environmental damage, generally refers to hair in which all strands are not uniformly aligned. The degree of hair frizz (or frizziness) is defined by the alignment of each hair strand relative to the surrounding hair strands. The present disclosure is also useful for shaping and straightening frizzy hair strands into a desired absolute directionality defined straightness or waviness of a population of individual (or bulk) hair strands. The present disclosure is also useful for shaping and straightening frizzy hair strands into a desired absolute directionality defined straightness or waviness of a population of individual (or bulk) hair strands.

The peptide sequences have at least one amino acid difference from SEQ ID NO: 1 and are typically capable of binding to keratin. It is believed that the amino acid sequence KKVELFPK (SEQ ID NO: 2.), is responsible for SEQ ID NO: 1's binding to hair keratin. In the disclosed peptides, any one or more of the amino acids in the amino acid sequence of SEQ ID NO: 1 and SEQ ID NO:2, can be replaced or substituted with cysteine.

In some examples, the total cysteine content of a disclosed peptide is less than 50% of SEQ ID NO. 1, less than 45% of SEQ ID NO. 1, less than 40% of SEQ ID NO. 1, less than 35% of SEQ ID NO. 1, less than 30% of SEQ ID NO. 1, less than 25% of SEQ ID NO. 1, less than 20% of SEQ ID NO. 1, less than 15% of SEQ ID NO. 1, less than 10% of SEQ ID NO. 1, less than 9% of SEQ ID NO. 1, less than 8% of SEQ ID NO. 1, less than 7% of SEQ ID NO. 1, less than 6% of SEQ ID NO. 1, or less than 5% of SEQ ID NO. 1.

Peptides having the amino acid sequence of any one of SEQ ID NOS: 3-SEQ ID NOS: 17, SEQ ID NOS: 18-SEQ ID NOS: 109, fragments and variants of any one of SEQ ID NO:1 and SEQ ID NOS: 3-SEQ ID NOS: 17, SEQ ID NOS: 18-SEQ ID NOS: 109, are provided and can be used individually or in combination in a hair composition such as those disclosed herein, known in the art, or designed by one of skill in the art. The fragments and variants can have, for example, at least 50%, 55%, 60%, 65%, 70%, 75%, 80%, 85%, 90%, or 95% sequence identity to any one of more of SEQ ID NO: 1 and SEQ ID NOS: 3-SEQ ID NOS: 17., SEQ ID NOS: 18-SEQ ID NOS: 109. The variants can include one or more amino acid substitution(s), addition(s), deletion(s), or a combination thereof relative to the reference peptide. The peptides typically include at least 1, preferably 2, 3, or more cysteines.

In some embodiments, the peptide is 10-50 amino acids in length, or any subrange there between inclusive, or any specific integer there between inclusive, including, but not limited to 10-45, 10-40, 10-35, 10-30, 10-29, 10-28, 10-27, 10-26, 10-25, 10-24, 10-23, 10-22, 10-21, 10-20, 10-19, 10-18, 10-17, 10-16, 10-15, 15-20, 15-21, 15-22, 15-23, 15-24, 15-25, 15-26, 15-27, 15-28, 15-29, 15-30, 18-27, 19-26, 20-25, or 21-24 amino acids inclusive, or 10, 11, 12, 13, 14, 15, 16, 17, 18, 19, 20, 21, 22, 23, 24, 25, 26, 27, 28, 29, or 30 amino acids.

Typically, the peptides can bind to hair and/or a keratin protein thereof. Preferably the peptides show improved binding and/or retention to hair, relative to a control peptide, such as SEQ ID NO: 1. Binding and/or retention of the peptide(s) can be measured, for example, by fluorescently labelling the peptide(s) and applying them to hair or keratin protein thereof and allowing them to bind to the hair and/or keratin protein thereof and subsequently subjecting the hair to repeated washings (i.e., shampoos). Comparison and statistical analysis of fluorescence imaging of the labeled peptides on the hair prior to washing and following at least one, 5, 10, 15, 20, 25, or 30 washings allows for determination of the degree of retention of the peptide(s) to the hair. In some embodiments, the hair is damaged hair. For example, in some embodiments, prior to testing binding and/or retention to the hair, the hair is damaged, such as by subjecting the hair to repeated bleaching treatments as described in Examples 8 and 9.

In some instances, binding and/or retention to the hair is demonstrated by fluorescently labeling a peptide and applying the labeled peptide the hair. Next the hair is washed one or more times and retention of the labeled peptide to washing is measured, such as by fluorescence imaging, and compared at one washing and at ten washings, optionally at 15 washings, at 20 washings, or more. In some instances, there is no significant difference (less than 5% reduction in fluorescence) in retention (the amount of peptide retained in the hair) after one washing compared to retention after ten washings. In some instances, the percent reduction in retention is less than about 50%; when comparing fluorescence detected after one washing to the fluorescence detected after ten washings. The same washing test can be conducted for any of the peptides described herein to determine the degree of retention of the peptides in the hair, and their retention ability. In some embodiments, prior to testing binding and/or retention to the hair, the hair is damaged, such as by subjecting the hair to repeated bleaching treatments as described in Examples 8 and 9.

In some embodiments, the peptides can be used at a reduced concentration to achieve the same or an improved results, as compared to a control such as SEQ ID NO: 1. For example, in some embodiments, the concentration of the peptide(s) is about less than 95% wt, about less than 90% wt, about less than 85% wt, about less than 80% wt, about less than 75% wt, about less than 70% wt, about less than 65% wt, about less than 60% wt, about less than 55% wt, about less than 50%, wt about less than 45% wt, about less than 40% wt, about less than 35% wt, about less than 30% wt, about less than 25% wt, about less than 20% wt, about less than 15% wt, about less than 10% wt, about less than 5%, wt about 0.01 to about 0.1% wt of the effective concentration of the peptide corresponding to SEQ ID NO. 1 used for hair straightening or shaping, or used for other common hair treatments, and/or binding to keratin or hair and/or improving the strength, look, or feel of hair.

In some embodiments, the peptide has one or more of the amino acid residues corresponding to SEQ ID NO 2 of SEQ ID NO. 1 replaced with a cysteine amino acid residue. To derive the peptide one or more glutamine (Q) amino acid residues of SEQ ID NO. 1, in any combination, replaced or substituted with a cysteine, one or more valine (V) amino acid residues of SEQ ID NO. 1, in any combination, replaced or substituted with a cysteine, one or more alanine (A) amino acid residues of SEQ ID NO. 1, in any combination, replaced or substituted with a cysteine, and/or one or more serine (S) amino acid residues of SEQ ID NO. 1, in any combination, replaced or substituted with a cysteine. In some embodiments, one or more of glutamine, valine, alanine, and serine amino acid residues of SEQ ID NO. 1, in any combination, each replaced or substituted with a cysteine.

In some embodiments, the peptide includes the addition of cysteine residues to either or both of the N- or C-terminus of any of SEQ ID NOS. 1 or 3-109. In some embodiments, there are ten cysteine amino acid residues added to the N-terminus of any of SEQ ID NOS. 1 or 3-17 and 18-109, or a variant thereof, nine cysteine amino acid residues added to the N-terminus of any of SEQ ID NOS. 1 or 3-16, and 18-109, or a variant thereof, eight cysteine amino acid residues added to the N-terminus of any of SEQ ID NOS. 1 or 3-17, and 18-109, or a variant thereof, seven cysteine amino acid residues added to the N-terminus of any of SEQ ID NOS. 1 or 3-17 and 18-109, or a variant thereof, six cysteine amino acid residues added to the N-terminus of any of SEQ ID NOS. 1 or 3-17 and 18-109, or a variant thereof, five cysteine amino acid residues added to the N-terminus of any of SEQ ID NOS. 1 or 3-17 and 18-109, or a variant thereof, four cysteine amino acid residues added to the N-terminus of any of SEQ ID NOS. 1 or 3-17 and 18-109, or a variant thereof, three cysteine amino residues added to the N-terminus of any of SEQ ID NOS. 1 or 3-17, or a variant thereof, two cysteine amino acid residues added to the N-terminus of any of SEQ ID NOS. 1 or 3-17 and 18-109, or a variant thereof, or one cysteine amino acid residue is added to the N-terminus of any of SEQ ID NOS. 1 or 3-17 and 18-109, or a variant thereof. In some embodiments, there are ten cysteine amino acid residues added to the C-terminus of any of SEQ ID NOS. 1 or 3-17 and 18-109, or a variant thereof, nine cysteine amino acid residues added to the C-terminus of any of SEQ ID NOS. 1 or 3-17 and 18-109, or a variant thereof, eight cysteine amino acid residues added to the C-terminus of any of SEQ ID NOS. 1 or 3-17 and 18-109, or a variant thereof, seven cysteine amino acid residues added to the C-terminus of any of SEQ ID NOS. 1 or 3-17 and 18-109, or a variant thereof, six cysteine amino acid residues added to the C-terminus of any of SEQ ID NOS. 1 or 3-17 and 18-109, or a variant thereof, five cysteine amino acid residues added to the C-terminus of any of SEQ ID NOS. 1 or 3-17 and 18-109, or a variant thereof, four cysteine amino acid residues added to the C-terminus of any of SEQ ID NOS. 1 or 3-17 and 18-109, or a variant thereof, three cysteine amino residues added to the C-terminus of any of SEQ ID NOS. 1 or 3-17 and 18-109, or a variant thereof, two cysteine amino acid residues added to the C-terminus of any of SEQ ID NOS. 1 or 3-17 and 18-109, or a variant thereof, or one cysteine amino acid residue is added to the C-terminus of any of SEQ ID NOS. 1 or 3-17 and 18-109, or a variant thereof. Any ten or less of cysteine amino acid residues added to the C-terminus of SEQ ID NO. 1 can be in any combination with any ten or less of cysteine amino acid residues added to the N-terminus of SEQ ID NO. 1.

Peptides of SEQ ID NO: 3 through SEQ ID NO: 17 and 18-109 or a variant thereof were modified with cysteine substitutions at various positions relative to SEQ ID NO: 1. Peptides having a Q13C or H6C and at least one additional cysteine substitution showed increased retention to hair after 10 shampoos when compared to peptides not having at least a Q13C or H6C substitution. The location of the amino acid cysteine substitution on the outside region of the peptide alpha helix in a position similar to the Q13C and H6C positions may play a role in the increased retention to hair after multiple shampoos.

The peptides as disclosed can be combined with one or more cosmetically acceptable carriers (i.e., water or aqueous solutions) and/or cosmetically acceptable excipients that are considered safe and effective to human hair and/or human scalp and may be administered to an individual's hair without causing undesirable biological side effects, such as burning, itching, and/or redness, or similar adverse reactions. The compositions may further contain an excipient that renders the formulations neutral pH, or a pH from about 5 to about 8. The composition may be a hair composition of any suitable form. Non-limiting examples may be in the form of low to moderate viscosity liquids, lotions, milks, oils, masks, mousses, sprays, gels, creams, shampoos, conditioners, and the like. Suitable excipients, such as those listed below, can be included or excluded from the hair care composition, depending on the form of use of the composition (e.g., hair spray, cream, conditioner, or shampoo).

The peptides as disclosed can be combined with one or more cosmetically acceptable ingredients. One of skill in the art would determine the proper ratio and combination of ingredients, including, but not limited to, surfactants, preservatives, chelating agents (such as ethylenediaminetetraacetic acid; trisodium ethylenediamine disuccinate), vitamins (such as vitamin E or C), proteins, film formers, detergents, resins, hair fixatives, opacifying agents, volatiles, propellants, acidifying agents (such as ascorbic acid, citric acid), alkalizing agents (such as sodium hydroxide, sodium carbonate) pH adjustors (such as citric acid, sodium hydroxide, phosphoric acid, etc.), neutralizing agents, hydrolyzing agents, liquid vehicles, carriers, anti-frizz agents, absorbents, emulsifiers, softeners, solubilizers, moisturizers, humectants, hydrolyzed proteins, reconstructors, acidifiers, acidity regulators, detanglers, polymers, glossers, lubricants, sequestrants, antistatic agents, sunscreens, thermal protectors, conditioners, buffers, stabilizers, thickeners, salts, emollients, antioxidants, alcohols, polysorbates, PEGs, polyquaternium polymers (such as, polyquaternium-7, polyquaternium-11, polyquaternium-113), quarternary ammonium compounds, fragrances, dyes or colors, oils, esters, fatty acids, bioactive additives, silicones, and an aqueous carrier. In some instances, the peptides are present in a composition containing water, hair conditioning agent(s), pH adjustors and/or buffering agent(s), chelating agent(s), preservative(s), surfactant(s), moisturizers or lubricating agent(s), and emollients. The cosmetically acceptable excipients, as may be present, can typically be present in an amount ranging from about 10 wt % to about 99.99 wt % of the composition, about 40 wt % to about 99 wt %, or from about 80 wt % to about to about 99 wt %.

In some embodiments, the composition includes an effective amount of peptide(s) to improve one or more aspects of hair's strength, visual appearance (i.e., sheen), or tactile properties (i.e., feel), or alter its shape or body compared to, for example, untreated hair or hair treated with an equivalent amount of a control peptide such as SEQ ID NO: 1.

Hair breakage is a significant problem encountered during coloring, bleaching, and other hair treatments. In some instances, the compositions described herein can improve hair quality by decreasing hair breakage when the hair is subjected to treatments, such as coloring, bleaching, straightening or permanent waving. In some instances, use of the disclosed peptide(s) and compositions thereof can reduce hair breakage by at least about 5, 10, 15, 20, 25, 30, 35, 40, 45, or 50% or higher after treatment with the peptides, as compared to untreated hair from the same individual. Standard methods of measuring hair breakage are known and involve use of repeated hair grooming experiments—whereby the number of broken hair fibers are recorded as a function of repeated combing/brushing strokes. For example, see T. A. Evans & K. Park, A statistical analysis of hair breakage. II. Repeated grooming experiments. J. Cosmet. Sci., 61, 439-455, 2010.

The peptide(s) disclosed herein may comprise a lipid conjugated to the site for bioconjugation. For example, the site for bioconjugation can be the amino acid sequence AKT, where the lipid is conjugated to the lysine of the amino acid sequence AKT. Any suitable lipids can be conjugated to peptides disclosed herein. Examples include, but are not limited to, myristoleic acid/alcohol/amine, palmitoleic acid/alcohol/amine, sapienic acid/alcohol/amine, oleic acid/alcohol/amine, elaidic acid/alcohol/amine, vaccenic acid/alcohol/amine, linoleic acid/alcohol/amine, linoelaidic acid/alcohol/amine, alpha linolenic acid/alcohol/amine, arachidonic acid/alcohol/amine, eicosapentaenoic acid/alcohol/amine, erucic acid/alcohol/amine, caprylic acid/alcohol/amine (octanoic acid/alcohol/amine), lauric acid/alcohol/amine, myristic acid/alcohol/amine, palmitic acid/alcohol/amine, lignoceric acid/alcohol/amine, arachidic acid/alcohol/amine, stearic acid/alcohol/amine, and sphingolipids including ceramide, sphingosine, sphingomyelin, alpha cerebroside, gangliosides, sulfatides, and phytosphingosine. The peptide compositions disclosed herein may be useful as daily or frequent use products including but not limited to shampoos, conditioners, gels, mousses, pomades, anti-frizz agents, sprays, or hair dyeing products that may be applied to the hair as part of customary hair care procedures including washing, conditioning, dyeing, drying, and styling. These compositions may be for use in a salon. In some embodiments, the peptide compositions may be suitable for home use The peptide compositions may be liquids, solids, or gels, and can be filled and stored in any suitable container, including bottles, cartons, tubes, and canisters. The peptide compositions may also be provided or used as part of a kit. In some embodiments, the kit is a hair straightening kit, a hair coloring kit, hair bleaching kit, or hair shaping kit. The kits may further include a developer (aqueous hydrogen peroxide), bottle, gloves, shampoo, conditioner, and/or an odor eliminator. Instructions for use of the kits are also typically provided. In the cases of coloring or bleaching kits, typically the kits contain more than one container (or more than one compartment in a given container) to ensure that the lightening agents (e.g., peroxides, bleach powders) or the coloring agent are stored separately from the peptide containing composition. The kits can optionally contain shampoos and conditioners.

The peptides disclosed herein can be made by expression in cells. The peptides can be produced in cells such as bacterial or yeast cells, Examples include, but are not limited to, *E. coli* and *Saccharomyces cerevisiae*; Standard methods of cell production are well known to one of skill in the art. Steps include:
1. cloning a sequence encoding the peptides into an expression plasmid;
2. introducing the recombinant expression plasmid into a cell;
3. expressing the peptide in the cell; and
4. isolating the peptide from the cell.

Alternatively, the peptide can be synthesized using chemical synthesis according to standard synthetic protocols.

The peptides disclosed herein can be used to straighten or shape a subject's hair as part of a hair composition. The peptides disclosed herein can be applied, typically as part of a composition, by hand, applicator bottle, applicator brush, dropper, spray bottle, or by any other suitable method and/or applicator.

The subject could be any mammal, preferably a human.

A typical hair straightening or shaping treatment generally includes two or three primary steps, performed in conjunction with manual fixing of the hair into a desired final form (for example, using "curlers", etc., and other shape forming tools as known in the art):
1. hair keratin relaxation, in which a hair keratin relaxation composition is applied to the hair of a subject and disulfide bonds present in the hair are broken;
2. application, in which the peptide of the present disclosure or hair composition thereof is applied to the hair; and
3. fixation, in which new disulfide bonds are reformed in the hair.

In some cases, step 2 and step 3 may be combined into a single step or step 2 and step 3 may occur simultaneously. In some other instances, fixation (step 3) may be performed after relaxation (step 1) and then application of the peptides (step 2) is performed. Each step can involve application of a solution to hair for about 5, 10, 15, 20, 25, or 30 minutes, though this time may range anywhere from approximately 5 minutes to 1 hour. In some instances, the hair relaxation composition is applied to the hair for a processing period ranging from about 10 to 15 mins, 35 to 45 mins, 45 to 60 mins, or 25 to 35 mins. In some cases, shorter processing times, such as from about 10 to 15 mins, may be used depending on existing damage to the hair, such as if it was previously bleached. In some cases, the peptides or hair composition thereof (step 2) are applied to the hair for a processing period of about 5 minutes. Any step can also optionally be repeated more than once. Hair can optionally be washed and dried before or after any step.

The hair keratin relaxation composition (of step 1) or the peptides or hair composition thereof (of step 2) can be applied using a brush and/or comb. Optionally, all the hair fibers being straightened or shaped are wetted by the compositions used to ensure the hair fibers are saturated. Optionally, following steps 1, 2, and 3, a leave-in conditioner may be applied to the hair for a processing period of at least about 5 minutes followed by optionally drying the hair.

A variety of different methods may be used for relaxation (step 1) and fixation (step 3). In step 1, any of the following may be used to break disulfide bonds: (1) heat; (2) applying a lye relaxer (e.g., sodium hydroxide solution at pH 12-14); (3) applying a no-lye relaxer (e.g., calcium hydroxide or guanidine carbonate at pH 9-11); (4) applying a "thio" relaxer (e.g., sodium thioglycolate, ammonium thioglycolate, dithiothreitol, thioglycolic acid, thiolactic acid, dihydrolipoate, thioglycerol, mercaptopropionic acid, pegylated thiols); (5) applying a natural, thiol-bearing compound (e.g., glutathione, cysteine, cysteinyl-glycine) optionally along with ascorbic acid or its derivates, preferably in a mildly basic solution (e.g., pH 9-10); or (6) applying an enzyme known to play a role in reducing keratin disulfide bonds with its necessary substrate(s) (e.g., glutathione reductase, cysteine dioxygenase, alkyl hydroperoxide reductase, thioredoxin reductase, dihydrolipoyl dehydrogenase, peptide methionine sulfoxide reductase, phospho-adenosine phosphosulfate reductase, ribonucleoside-diphosphate reductase). Non-thio relaxers are also known and may used in lieu of "thio" relaxers including, but not limited to, alkaline hydroxides (i.e., sodium hydroxide, potassium hydroxide), sodium bisulfite, ammonium bisulfite, zinc formaldehyde sulfoxylate, sodium formaldehyde sulfoxylate, sodium metabisulfite, potassium borohydride, and hydroquinone.

For fixation, as takes place in step 3, any of the following may be used to form or reform disulfide bonds: (1) applying sufficient heat; (2) application of an acid or acidic solution; (3) application of hydrogen peroxide; (4) application of any oxidase enzyme that produces hydrogen peroxide with its necessary substrate(s) (e.g., glucose oxidase, etc.); and/or (5) not washing the hair for at least 24 hours after step 2, optionally also adding a conditioning agent to the hair. In some instances, applying sufficient heat to the hair during fixation can involve blow drying and/or flat ironing the hair at a temperature ranging from about 375 to about 410° F. or about 350 to about 375° F. using a suitable number of passes, such as about 5 to 8 passes. In some cases, lower heating temperatures may be used depending on existing damage to the hair, such as if it was previously bleached.

Personal care and hair compositions usually contain conventional cosmetically acceptable excipients which may be used, for example, to modify various properties of the composition and to improve aesthetics. Such cosmetically acceptable excipients are described above. Commonly used natural and synthetic excipients are described, for example, in International Cosmetic Ingredient Dictionary and Handbook, Twelfth Edition 2008, ISBN-10: 1882621433, (hereinafter "Cosmetic Handbook") and CTFA ingredient information (http://www.ctfa-online.org/pls/ctfa_online.home), the content of which is hereby incorporated by reference in its entirety.

Emulsifiers are typically used to help blend ingredients which otherwise would be immiscible. Emulsifiers may be synthetic or natural. Natural emulsifiers may include, but are not limited to, olive oil, olive oil/wheat protein, olive oil/oat protein, sucrose esters, rice bran emulsifiers and/or various other food and pharmaceutical grade emulsifiers, alone or in combination.

Synthetic emulsifiers may include, but are not limited to, silicone emulsifiers, such as dimethicone copolyols; sulfonates and sulfonic acid derivatives; phosphorous organic derivatives; sugar esters; fatty esters, such as sorbitan monolaurate, sorbitan stearate, sorbitan laurate, sorbitan palmitate, sorbitan oleate; polyesters/PEG (polyethylene glycol) derivatives, such as Polysorbate 20 (polyethylene glycol 20 sorbitan monolaurate); fatty acid esters of fatty alcohols, such as glyceryl stearate, isopropyl stearate, hexyl laurate; fatty acid amides; acyl lactylates; alkoxylated compounds, such as alkoxylated block polymers, alcohols, alkylphenols, amines, amides, fatty esters, fatty acids, oils, sugar esters and polyesters, fatty acid esters of fatty alcohols, and ethers of fatty alcohols; carboxylated alcohol ethoxylates and alkylphenol ethoxylates; carboxylic acides/fatty acids, and mixtures thereof. Other suitable emulsifiers can include, but are not limited to, copolymers of an unsaturated ester and styrene sulfonate monomer, dicetyl phosphate, cetearyl alcohol, glyceryl ester, polyoxyethylene glycol ether of cetearyl alcohol, stearic acid, polysorbate-20, ceteareth-20, lecithin, glycol stearate, polysorbate-60, polysorbate-80, or combinations thereof. More than one emulsifier may be included in the formulation. Still other natural and synthetic emulsifiers may be found in the Cosmetic Handbook.

Colorants are typically used to provide relatively uniform color to the final cosmetic composition. Colorants may be synthetic or natural. Natural colorants may include pigments or plant-derived colors. Natural pigments may be inorganic (mineral) or organic, white or non-white, and coated or uncoated particles. Natural colorants may include, for example, cerium oxide, chromium oxide, iron oxide, titanium dioxide, zinc oxide, zirconium oxide, carbon black, chromium, chromium hydroxide green, ferric blue, manganese violet, ultramarine blue, D&C and FD&C colors, azo, indigoid, insoluble metallic salts of certified color additives, referred to as the Lakes, and the like, and mixtures thereof.

Synthetic colorants may include, for example, triphenylmethane, anthraquinone, and xanthine dyes and mixtures thereof. Other natural and synthetic colorants may be found in the Cosmetic Handbook and CTFA ingredient information.

Compositions may include waxes. Waxes may be synthetic or natural. Natural waxes may include, for example, beeswax, carnauba wax, and/or candelilla wax, hydrogenated jojoba oil, hydrogenated jojoba wax, hydrogenated microcrystalline wax, hydrogenated rice bran wax. Synthetic waxes may include, for example, cetyl esters, montan acid wax, paraffin, PEG-6 beeswax, PEG-8 beeswax, sulfurized jojoba oil, synthetic beeswax, synthetic candelilla wax, synthetic carnauba wax, synthetic japan wax, synthetic jojoba oil, synthetic wax, stearoxy dimethicone, dimethicone behenate, stearyl dimethicone, and synthetic homo- and copolymer waxes from the ethylene series or mixtures thereof. Other natural and synthetic waxes and oils may be found in the Cosmetic Handbook and CTFA ingredient information.

Compositions also may include preservatives. Preservatives may be either synthetic or natural and may be used to inhibit growth of undesirable microorganisms. Natural preservatives may include black currant fruit extract, aspen bark, radish root, and sorbic acid, alone or in combination.

Synthetic preservatives may include, for example, methylparaben, ethylparaben, propylparaben, imidazolidinyl urea, diazolidinyl urea, DMDM hydantoin, isothiazolinones, chlorinated aromatic compounds, para-hydroxybenzoic acids/parabens, alone or in combination. Other suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), propanediol, sodium benzoate, ethylenediaminetetraacetic acid (EDTA), behentrimonium chloride, potassium sorbate, and/or grapefruit seed extract, or combinations thereof. More than one preservative may be included in the compositions. Other preservatives are known in the cosmetics industries and include salicylic acid, DMDM Hydantoin, Formaldahyde, Chlorphenesin, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol). Still other natural and synthetic preservatives may be found in the Cosmetic Handbook and CTFA ingredient information. In some instances, the preservative(s) are optionally included in an amount ranging from about 0.1% to about 5% by weight of the composition or from about 0.3% to about 3% by weight of the composition. Preferably, the compositions disclosed are paraben free.

Compositions also may include thickeners. Thickeners may either be synthetic or natural. Thickeners may be used to gel or thicken cosmetic compositions to provide, for example, better deposition properties. Natural thickeners may include waxes, gums and powders and mixtures thereof. Natural waxes may include beeswax, carnauba, and/or candelilla and mixtures thereof. Natural gums may include acacia, xanthan, schelortium (amigel), and/or cellulose and mixtures thereof. Natural powders may include clay, diatomaceous earth, fuller's earth, silica, silica shells or spherical silica, fumed silica, spherical silica, hydrated silica, silica silylate, mica, titanated mica, talc, cellulose or spherical cellulose beads, microcrystalline cellulose, corn starch, rice starch, glyceryl starch, soy flour, walnut shell powder, agar, sericite, dextran, nylon, silk powder, chalk, calcium carbonate, bismuth oxychloride, iron oxide, titanium dioxide, aluminum silicate, magnesium aluminum silicate, calcium silicate, magnesium trisilicate, aluminum starch octenylsuccinate, bentonite, hectorite, kaolin, maltodextrin, montmorillonite, zinc laurate, zinc myristate, zinc rosinate, alumina, attapulgite, tin oxide, titanium hydroxide, trimagnesium phosphate, or mixtures thereof.

Synthetic thickeners may include, for example, AMP isostearoyl hydrolyzed collagen, AMP isostearoyl hydrolyzed wheat protein, cetyl hydroxyethylcellulose, chondroitin sulfate, cocoamidopropyldimethylamine $C_{8-16}$ isoalkysuccinyl lactoglobulin sulfonate, cocodimonium hydroxypropyl hydrolyzed collagen, distarch phosphate, ethyl ester of hydrolyzed animal protein, guar hydroxypropyltrimonium chloride, hydrolyzed animal or plant protein, hydroxypropyl guar, hydroxypropylmethyl cellulose, hydroxypropyl cellulose, hydroxyethyl cellulose, isostearoyl hydrolyzed collagen, methylcellulose, nitrocellulose, nonoxynyl hydroxyethylcellulose, acrylate polymers, acrylamine polymers, acrylic acid polymers (carbomer), PVM/MA Decadiene crosspolymers, polyvinylpyrrolidone polymers, silicone oils, polyethylene thickeners, aluminum starch octenyl succinate, trihydroxystearin, and mixtures thereof. Other natural and synthetic thickeners may be found in the Cosmetic Handbook and CTFA ingredient information.

Compositions may include conditioning agents or treatment agents. Conditioning or treatment agents may be either synthetic or natural. Natural conditioning or treatment agents may include panthenol, vitamins, lauroyl lysine, isostearic acid, lecithin, soft emollient waxes, fruit/botanical complexes, sweet almond oil, coconut oil, jojoba blends, honey, seaweed/algae, aloe, acai extract, wild pansy extract, lotus extract, papaya extract, zuzu extract, and/or orchid extract. Other suitable conditioning agents can include, but are not limited to, silicone-based agents (e.g., silicone quaternium-8), hydrolyzed wheat and/or soy protein, amino acids (e.g. wheat amino acids, arginine), rice bran wax, meadowfoam seed oil, mango seed oil, grape seed oil, jojoba seed oil, sweet almond oil, hydroxyethyl behenamidopropyl dimonium chloride, aloe leaf extract, aloe barbadensis leaf juice, phytantriol, retinyl palmitate, behentrimonium methosulfate, cyclopentasiloxane, quaternium-91, stearamidopropyl dimethylamine, and combinations thereof. In some instances, the conditioning agent(s) are optionally included in an amount ranging from about 0.1% to about 5% by weight of the composition or from about 0.3% to about 3% by weight of the composition.

Synthetic conditioning and treatment agents may include, for example, mercaptyl-containing compounds, such as mercapto-containing quaternary nitrogen compounds; betaine/aliphatic organic acid; silicone oil, silicone gum, silicone polymers, fatty acids, esters of fatty acids, fatty alcohols, ethoxylates, polyol polyesters, glycerine, glycerin monoesters, glycerin polyesters, cholesterol esters, polyolefinic glycols, polyolefinic monoester, polyolefinic polyesters. Other natural and synthetic conditioning and treatment agents may be found in the Cosmetic Handbook and CTFA ingredient information.

Compositions also may include one or more essential and natural oils. Essential oils may be synthetic or natural. Natural essential oils may include bergamot, chamomile german, chamomile maroc, chamomile roman, cinnamon zeylanicum, clove buds, *eucalyptus globulus*, frankincense, fennel, hyssop, juniper, lemon grass, mountain savory, niaouli, red thyme, rosemary, rose geranium, tagestes, and ylang ylang. Natural oils may include, for example, jojoba oil, sweet almond oil, coconut oil, shea butter, mango butter, and/or aloe vera butter or mixtures thereof.

Synthetic essential oils may include, for example, esters, such as acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, PEG-4 diheptanoate, hydrogenated castor oil, isotridecyl isononanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, tridecyl octanoate, octyl palmitate, dioctyl malate, tridecyl octanoate, myristyl myristate, octododecanol; fatty alcohols such as oleyl alcohol, isocetyl alcohol; and also silicone oils, isoparaffins, hydrogenated polyisobutene, petrolatum, lanolin derivatives, and sorbitan derivatives. Other natural and synthetic oils may be found in the Cosmetic Handbook and CTFA ingredient information.

Composition also may include one or more herbs and/or extracts and/or filtrates of herbs, such as, for example, Acacia *Catechu, Acanthopanax* Gracilistylus, Cacsalpinia *Sappan*, Epimedium *Spinosa, Paeonia lactiflora, Paeonia obovata, Atractylodes macrocephala, Glycyrrhiza uralexisis, Glycyrrhiza glabra, Lycium chinense*, Nauclea rhyncholphylla, Cinnainomum *cassia, Astragalus membranaceus, Scutellaria baicalensis, Schizonepeta tenuifolia, Ephedra sinica, Ophiopogon japonicus, Paeonia suffruticosa, Artemisia annua, Aretemisia apiacea, Panax notoginseng, Cornus officinalis*, Acorius gramineus, Reluhania *glutinosa, Gastrodia elata*, Asparagus cochiichinensis, Cuscuta *chinensis, Schizandra chinensis, Schizandra spenanthera, Magnolia* liliflora, Epimedium brevicomum, Epimedium grandiflorun, Epimedium sagittatum, Houttuynia *cordata, Polygala tenuifolia*; and *Perilla frutescens*, and an Aloe Vera extract, alone or in any combination.

Compositions also may include one or more plant seeds and/or extracts and/or filtrates of plant seeds obtained from a plant such as, for example, rapeseed(*Brassica* spp.), soybean (*Glycine max*), sunflower (Lianthus *annuus*), oil palm (*Elaeis* guineeis), cottonseed(*Gossypium* spp.), groundnut (*Arachis hypogaea*), coconut(*Cocus nucifera*), castor (*Ricinus communis*), safflower (Carthamus tinctorius), mustard(*Brassica* spp. and *Sinapis alba*), coriander, (*Coriandrum sativum*), squash(*Cucurbita maxima*), linseed/flax (*Linum usitatissimum*), Brazil nut (Bertholletia *excelsa*) jojoba(*Simmondsia chinensis*) and maize(*Zea mays*), alone or in combination.

The composition can also include one or more surfactants that are able to reduce the surface tension of water and cause the hair formulation to slip across or onto the skin or hair. Surfactants also include detergents and soap. The surfactants may be amphoteric, anionic, or cationic. Suitable surfactants that may be used in the formulation include, but are not limited to, heptyl glucoside, 3-aminopropane sulfonic acid, almond amide, almond amidopropyl betaine, almond amidopropylamine oxide, aluminum hydrogenated tallow glutamate, aluminum lanolate, aminoethyl sulfate, aminopropyl lauryl glutamine, ammonium C12-15 alkyl sulfate, ammonium C12-15 pareth sulfate, C12-16 alkyl ammonium sulfate, ammonium C9-10 perfluoroalkylsulfonate, ammonium capryleth sulfate, ammonium capryleth-3 sulfate, ammonium monoglyceride sulfate, ammonium sulfate, ammonium isothionate, ammonium cocoyl sarcosinate, ammonium cumene sulfonate, ammonium dimethicone copolyol sulfate, ammonium dodecylbenzenesulfonate, ammonium isostearate, ammonium laureth sulfate, ammonium laureth-12 sulfate, ammonium laureth-5 sulfate, ammonium laureth-6 carboxylate, ammonium laureth-7 sulfate, ammonium laureth-8 carboxylate, ammonium laureth-9 sulfate, ammonium lauroyl sarcosinate, ammonium lauryl sulfate, ammonium lauryl sulfosuccinate, ammonium myreth sulfate, ammonium myristyl sulfate, ammonium nonoxynol-30 sulfate, ammonium nonoxynol-4 sulfate, ammonium oleate, ammonium palm kernel sulfate, ammonium polyacrylate, ammonium stearate, ammonium tallate, ammonium xylene sulfonate, ammonium xylene sulfonate, amp-isostearoyl gelatin/keratin amino acids/lysine hydroxypropyltrimonium chloride, amp-isostearoyl hydrolyzed collagen, apricot kernel oil PEG-6 esters, apricot amide, apricot amidopropyl betaine, arachideth-20, avocadamide, avocadamidopropyl betaine, babassuamide, babassuamidopropyl betaine, babassuamidopropylamine oxide, behenalkonium chloride, behenamide, behenamide, behenamidopropyl betaine, behenamine oxide, sodium laureth sulfate, sodium lauryl sulfate, a polyoxyether of lauryl alcohol or ceteareth-20, or combinations thereof. More than one surfactant may be included in the composition. The surfactants are optionally included in an amount ranging from about 0.1% to about 15% by weight of the formulation or about 1% to about 10% by weight of the composition.

Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, ammonyx cetac, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-β-iminodipropionate, myristoamphoacetate, lauryl betaine and lauryl sulfobetaine.

The composition can also include one or more emollients that can protect against wetness or irritation, soften, soothe, coat, lubricate, moisturize, protect, and/or cleanse. Suitable emollients for use in the composition can include, but are not limited to, isodecyl neopentanoate, a silicone compound (e.g., dimethicone, cyclomethicone, dimethicone copolyol or a mixture of cyclopentasiloxane and dimethicone/vinyldimethicone cross polymer, cyclopentasiloxane polysilicone), polyols such as sorbitol, glycerin, propylene glycol, ethylene glycol, polyethylene glycol, caprylyl glycol, polypropylene glycol, 1,3-butane diol, hexylene glycol, isoprene glycol, xylitol; ethylhexyl palmitate; a triglyceride such as caprylic/capric triglyceride and fatty acid ester such as cetearyl isononanoate or cetyl palmitate. In a specific embodiment, the emollient is dimethicone, amidodimethicone, dimethiconol, cyclopentasiloxane, potassium dimethicone PEG-7 panthenyl phosphate, cetyl stearyl alcohol, cetyl alcohol, cetearyl alcohol, or combinations thereof. More than one emollient may be included in the composition. The emollient can be optionally included in an amount ranging from about 0.5% to about 15% by weight of the formulation or from about 1% to about 10% by weight of the composition.

The composition can also include one or more diluents. Water is the preferred diluent. The composition typically contains greater than one percent (by weight) water, preferably greater than five percent (by weight) water, more preferably greater than 50% (by weight) water, and most preferably greater than 80% (by weight) water. Alcohols, such as ethyl alcohol and isopropyl alcohol, may be used at low concentrations (about 0.5% by weight of the formulation) to enhance hair penetration and/or reduce odor.

The composition can also include one or more viscosity modifying agents, such as viscosity increasing agents. Classes of such agents include, but are not limited to, viscous liquids, such as polyethylene glycol, semisythetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof.

The composition can also include one or more antioxidants. Examples include, but are not limited to, tocopheryls, BHT, ascorbic acid, *Camellia sinensis* leaf extract, ascorbyl palmitate, magnesium ascorbyl phosphate, carotenoids, resveratrol, triethyl citrate, arbutin, kojic acid, tetrahexydecyl ascorbate, superoxide dismutase, zinc, sodium metabisulfite, lycopene, ubiquinone, and combinations thereof.

The composition can also include one or more opacifying agents. Opacifying agents are added to the formulations to make it opaque. Suitable opacifying agents include, but are not limited to, glycol distearate and ethoxylated fatty alcohols.

The composition may be in the form of a spray. The spray typically includes the peptides and a cosmetically acceptable carrier. In some embodiments, the carrier is water or a water and alcohol mixture. The spray formulation optionally includes an antioxidant, sunscreen agent, vitamin, protein, peptide, plant extract, humectant, oil, emollient, lubricant, thickener, hair conditioning agent, polymer, and/or surfactant. The spray formulation can include a preservative. In some instances, the spray includes a fragrance. In some embodiments, the spray includes a surfactant. The hair spray formulations may be dispensed from containers that include aerosol dispensers or pump spray dispensers. Such dispensers are known in the art and are commercially available from a variety of manufacturers. When the spray composition is dispensed from a pressurized aerosol container, a propellant may be used to force the formulation out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed. The amount of propellant may range from about 10% to about 60% by weight of the spray composition. The propellant may be separated from the composition, as in a two-compartment container. Other suitable aerosol dispensers are those characterized by the propellant being compressed air, which can be filled into the dispenser using a pump or equivalent device prior to use. Conventional non-aerosol pump spray dispensers, i.e., atomizers, may also be used to apply the composition containing peptides to the hair.

In some instances, the composition may be in the form of a conditioner. The conditioner typically includes the peptides in a suitable carrier. Additionally, the conditioner may include cationic polymers derived from polysaccharides, for example cationic cellulose derivatives, cationic starch derivatives, cationic guar derivatives (such as guar hydroxypropyltrimonium chloride), cationic locust bean gum derivatives, synthetic cationic polymers, polyquaternium polymers (such as polyquaternium-7, polyquaternium-11, polyquaternium-113), and mixtures or combinations of these agents. The conditioner may comprise other synthetic or natural polymers or polymers derived from biological preparation processes, which are functionalized, where appropriate, for example with cationic or neutral groups. These polymers may have a stabilizing or strengthening action on the hair and/or a conditioning action (deposition on the surface of the hair).

In some instances, the composition may be in the form of a shampoo. The shampoo typically includes the peptides in a suitable carrier. The peptides may be included in any suitable concentration. Additionally, the shampoo may include from about 0.5% to about 20% by weight of a surfactant. Surfactants utilized in shampoo compositions are well-known in the art and are disclosed, for example, in U.S. Pat. No. 6,706,258 to Gallagher, et al. and U.S. Pat. No. 7,598,213 to Geary, et al.

In some cases, the peptides are in the form of liquid compositions. In these instances, the liquid compositions may contain any suitable concentration of the peptides, as described above, in a suitable carrier, typically a diluent, such as described above.

The peptides may be applied to hair, typically as part of a composition, following a hair treatment (i.e., a post-treatment application), such as a hair coloring, hair bleaching, permanent hair waving, hair straightening, or other common hair treatment. In some other instances, the peptides may be applied to hair, typically as part of a composition, prior to a hair treatment (i.e., a pre-treatment application), such as a hair coloring, hair bleaching, permanent hair waving, hair straightening, or other common hair treatment. Hair coloring is art understood to refer to treatments that modify the color of hair, such as using oxidative dyes and precursors thereof, or direct dyes. Hair bleaching is art understood to refer to treatments that remove color from hair such as by application of bleaching agents. Bleaching agents used in bleaching methods include applying a combination of developer (aqueous hydrogen peroxide) and bleach powder (a powder containing at least persulfate(s) and alkalizing agent(s)). The aforementioned treatments are well known to the person of skilled in the art. Following a treatment, the peptide containing composition, in any suitable form, can be applied on the same day or it may be applied later, such as within 1 to 2 weeks following treatment. The amount of the peptide containing composition applied can, in some instances, be sufficient to saturate the hair. The peptide containing composition may be applied to the hair as a single application, or application may be repeated one or more times. The volume of peptide containing composition applied to the hair in each application may be about 1 to about 100 ml per person depending on their length and volume of hair. In some embodiments, application of the peptide containing composition could be repeated immediately (e.g., within 10 to 15 seconds) or approximately 1, 5, 7.5, 10, 12.5, 15, 17.5, or 20 minutes after the first application. In some instances, it may be necessary to remove the peptide containing composition from the hair following an application, such as by rinsing and/or shampooing the hair following application, for example within 10, 15, 25, 30, 45, or 60 seconds, or within two, three, four, or five minutes after application. Alternatively, the peptide containing composition may be rinsed from the hair within about 30 minutes following application, between about 5 minutes and about 20 minutes, or about 10 minutes after application of the peptide containing composition to the hair, depending on hair type.

The above description is presented to enable a person skilled in the art to make and use the disclosed peptides and is provided in the context of a particular application and its requirements. Various modifications to the embodiments and aspects will be readily apparent to those skilled in the art, and the generic principles defined herein may be applied to other aspect, embodiments and applications without departing from the spirit and scope of the information disclosed herein. The examples herein are not intended to be limited to the aspects or embodiments described but are to be accorded the widest scope consistent with the principles and features disclosed herein. A further understanding can be obtained by reference to certain specific examples.

The following peptides were synthesized and provided by a commercial supplier (Genscript USA, Inc., Piscataway, NJ): SEQ ID NO: 3-SEQ ID NO: 108.

Example 1: Treatment with Heat Only

Tresses of curly Brazilian hair were cut into ½ inch wide samples. The tresses were then washed with shampoo and allowed to air dry. The hair was straightened using a flat iron at 460° F. Once the hair was visibly straight, the hair was wrapped tightly in aluminum foil. A flat iron was applied to a section of the wrapped hair by holding the flat iron to the section for 10 seconds. This process was repeated until all sections of the hair were flat ironed.

Six individual solutions of each peptide corresponding to SEQ ID NO. 3 through SEQ ID NO 8 were dissolved in de-ionized ("DI") water at a concentration of about 1 milligram per milliliter ("mg/mL") and then applied to separate hair samples until the hair sample was saturated. The saturated hair was allowed to sit for 1 hour at 37° C. The hair was then blow dried under medium heat while gently pulling the hair into a straight shape. A flat iron was then applied to the hair at 400° F.

The straightened hair was washed with shampoo and allowed to air dry, and this washing/drying procedure was repeated a total of 10 times. Following this treatment, each hair sample was significantly straightened compared to untreated samples, and small waves remained in the treated hair. There was little identifiable difference in efficacy among the six designed keratin binding peptides, although peptides corresponding to SEQ ID NO. 5 SEQ ID NO. 6, SEQ ID NO. 7 and SEQ ID NO. 8 showed a slightly higher straightening efficiency than SEQ ID NO. 3 and SEQ ID NO. 4.

Example 2: Treatment with Lye and Hydrogen Peroxide

Tresses of curly Brazilian hair were cut into ½ inch wide samples. The tresses were then washed with shampoo and allowed to air dry. The hair then soaked in a solution of sodium hydroxide pH 12 for 30 minutes at room temperature. After this time, the hair was rinsed with DI water. The hair was then blow dried under medium heat while gently pulling the hair into a straight shape. A flat iron was then applied to the hair at 400° F.

Six individual solutions of each designed keratin binding peptide corresponding to SEQ ID NO. 3 through SEQ ID NO. 8 were dissolved in in DI water at a concentration of 1 mg/ml and then applied to individual hair samples until the hair sample was saturated, and the hair sample was allowed to sit for 30 minutes at room temperature. The hair sample was then blow dried under medium heat while gently pulling the hair into a straight shape. A flat iron was then applied to the hair at 400° F.

L'Oreal® Oreor Creme 40 volume developer was then applied to the hair samples until the hair sample was saturated, and then allowed to sit for 30 minutes at room temperature. The hair samples were then rinsed with DI water.

Each straightened hair sample was washed with shampoo and allowed to air dry, and this washing/drying procedure was repeated a total of 10 times. Following this treatment, each hair sample was significantly straightened compared to untreated samples, and only slight waves remained in the treated hair. There was little identifiable difference in efficacy among the six peptides, although peptides corresponding to SEQ ID NO. 5, SEQ ID NO. 6, SEQ ID NO. 7 and SEQ ID NO. 8 showed a slightly higher straightening efficiency than SEQ ID NO. 3 and SEQ ID NO. 4.

Example 3: Treatment with Lye and Glucose Oxidase

Tresses of curly Brazilian hair were cut into ½ inch wide samples. The tresses were then washed with shampoo and allowed to air dry. The hair then soaked in a solution of sodium hydroxide pH 12 for 30 minutes at room temperature. After this time, the hair was rinsed with DI water. The hair was then blow dried under medium heat while gently pulling the hair into a straight shape. A flat iron was then applied to the hair at 400° F.

A solution of the peptide corresponding to SEQ ID. NO. 8 in DI water at a concentration of 1 mg/mL was then applied to hair sample until the hair sample was saturated, and the hair was allowed to sit for 30 minutes at room temperature. The hair was then blow dried under medium heat while gently pulling the hair into a straight shape. A flat iron was then applied to the hair at 400° F.

A solution of glucose oxidase (2 mg/mL) and glucose (18 mg/mL) in 50 mM sodium phosphate buffer pH 5.8 was then applied to the hair until the hair was saturated, and the hair was allowed to sit for 30 minutes at room temperature. The hair was then rinsed with DI water.

The straightened hair was washed with shampoo and allowed to air dry, and this washing/drying procedure was repeated a total of 10 times. Following this treatment, each hair sample was significantly straightened compared to untreated samples, and only slight waves remained in the treated hair.

Example 4: Treatment with Glutathione Reductase and Hydrogen Peroxide

Tresses of curly Brazilian hair were cut into ½ inch wide samples. The tresses were then washed with shampoo and allowed to air dry. The hair then soaked in a solution of glutathione reductase (0.01 mg/mL), glutathione (100 mg/mL), and nicotinamide adenine dinucleotide phosphate (0.083 mg/mL) in 50 mM sodium phosphate buffer pH 8 for 30 minutes at room temperature. After this time, the hair was rinsed with DI water. The hair was then blow dried under medium heat while gently pulling the hair into a straight shape. A flat iron was then applied to the hair at 400° F.

A solution of a peptide corresponding to SEQ ID NO. 8 in DI water at a concentration of 1 mg/mL was then applied to har until the hair was saturated, and the hair was allowed to sit for 30 minutes at room temperature. The hair was then blow dried under medium heat while gently pulling the hair into a straight shape. A flat iron was then applied to the hair at 400° F.

L'Oreal® Oreor Creme 40 volume developer was then applied to the hair until the hair was saturated, and the hair was allowed to sit for 30 minutes at room temperature. The hair was then rinsed with DI water.

The straightened hair was washed with shampoo and allowed to air dry, and this washing/drying procedure was repeated a total of 10 times. Following this treatment, each hair sample was significantly straightened compared to untreated samples, and only slight waves remained in the treated hair.

Example 5: Treatment with Glutathione and Glucose Oxidase

Tresses of curly Brazilian hair were cut into ½ inch wide samples. The tresses were then washed with shampoo and allowed to air dry. The hair then soaked in a solution of glutathione (100 mg/mL) in sodium hydroxide pH 9 for 30 minutes at room temperature. After this time, the hair was rinsed with DI water. The hair was then blow dried under medium heat while gently pulling the hair into a straight shape. A flat iron was then applied to the hair at 400° F.

A solution of the peptide corresponding to SEQ ID NO. 8 in DI water at a concentration of 1 mg/mL was then applied to hair until the hair was saturated, and the hair was allowed to sit for 30 minutes at room temperature. The hair was then blow dried under medium heat while gently pulling the hair into a straight shape. A flat iron was then applied to the hair at 400° F.

A solution of glucose oxidase (2 mg/mL) and glucose (18 mg/mL) in 50 mM sodium phosphate buffer pH 5.8 was then applied to the hair until the hair was saturated, and the hair was allowed to sit for 30 minutes at room temperature. The hair was then rinsed with DI water.

The straightened hair was washed with shampoo and allowed to air dry, and this washing/drying procedure was repeated a total of 10 times. Following this treatment, each hair sample was significantly straightened compared to untreated samples, and only slight waves remained in the treated hair.

Example 6: Treatment with Ammonium Thioglycolate and Hydrogen Peroxide

Tresses of curly Brazilian hair were cut into ½ inch wide samples. The tresses were then washed with shampoo and allowed to air dry. The hair then soaked in a solution of ammonium thioglycolate (10% v/v) in sodium hydroxide pH 10 for 30 minutes at room temperature. After this time, the hair was rinsed with DI water. The hair was then blow dried under medium heat while gently pulling the hair into a straight shape. A flat iron was then applied to the hair at 400° F.

In some samples, a solution of the peptide corresponding to SEQ ID NO. 8 in DI water at a concentration of 1 mg/mL was then applied to hair until the hair was saturated, and the hair was allowed to sit for 30 minutes at room temperature. In these samples, the hair was then blow dried under medium heat while gently pulling the hair into a straight shape. A flat iron was then applied to the hair at 400° F.

For all hair samples, a solution of hydrogen peroxide (2% v/v) was then applied to the hair until the hair was saturated, and the hair was allowed to sit for 30 minutes at room temperature. The hair was then rinsed with DI water.

The straightened hair was washed with shampoo and allowed to air dry, and this washing/drying procedure was repeated a total of 30 times. Following this treatment, the treated hair samples were significantly straightened compared to an untreated sample, and only slight waves remained in the treated hair.

The break force of treated hair samples was measured using a custom apparatus. Individual hairs were cut into 13-centimeter-long sections. Both ends of the hairs were wrapped in tape 1 centimeter from each end. The hair was then held in a vertical position between two clamps (top=fixed, bottom=movable) with 1-centimeter-long grips such that the grips were aligned with the taped ends of the hair. Force was gradually applied to the bottom clamp, and the force at break was recorded. Ten replicates were collected for each treatment group.

Example 7: Fluorescence Binding Studies

To a solution of 500 µL of DI water was added 1 mg of SEQ ID NO. 8. Then, a solution of 84 mg of sodium bicarbonate in 1 mL of DI water was prepared, and 12 µL of this solution was added to the SEQ ID NO. 8 solution. Immediately prior to conjugation, 1 mg of Alexa Fluor 647 NHS ester (Thermo Fisher Scientific) dye molecule was dissolved in 100 µL of DMSO, and 15 µL of this solution was added to the SEQ ID NO. 8 solution. After the dye was added, the solution was incubated at 4° C. in the dark for 16 hours. Removal of unbound dye molecules was carried out using a PD MiniTrap G-10 column (Cytiva) using DI water as the elutant. Fractions containing dye labeled SEQ ID NO. 8 were pooled.

Hair samples were then treated according to Example 6, except that treatment with SEQ ID NO. 8 was replaced with dye labeled SEQ ID NO. 8 while varying the peptide concentration), binding time, number of SEQ ID NO. 7 applications, or number of shampoos at the end of the treatment.

Fluorescence images were collected on a EVOS M7000 Imaging System (Thermo Fisher Scientific) using a Cy5 filter set. Images were collected using a 0.1 second exposure time at a light intensity of 0.0023.

Example 8: Comparative Tensile Studies

Swatches of Brazilian hair were bleached using BW2 hair powder lightener (bleach powder) (Clariol) and oreor creme 40 volume developer (aqueous hydrogen peroxide) (L'Oreal) mixed in a 1:2 ratio with constant stirring for 1 minute until the bleaching mixture became smooth and homogeneous. The hair swatches were saturated in the bleaching mixture and left to sit at room temperature for 45 minutes. The hair swatches were then rinsed with deionized water (DI) for 2 minutes, thoroughly shampooed, and allowed to air dry. The bleaching procedure was repeated two additional times to yield bleached Brazilian hair swatches.

Tresses of both virgin and bleached curly Brazilian hair were cut into ½ inch wide samples. The tresses were then washed with shampoo and allowed to air dry. The hair then soaked in a solution of cysteine (100 mg/mL) and ascorbic acid (10 mg/mL) in sodium hydroxide pH 10 for 30 minutes at room temperature. After this time, the hair was rinsed with DI water. The hair was then blow dried under medium heat while gently pulling the hair into a straight shape. A flat iron was then applied to the hair at 400° F.

In some samples, a solution of the peptide corresponding to SEQ ID NO. 1, SEQ ID NO. 8, SEQ ID NO. 9, or SEQ ID NO. 10 in DI water at a concentration of 1 mg/mL was then applied to hair until the hair was saturated, and the hair was allowed to sit for 30 minutes at room temperature. The hair was then blow dried under medium heat while gently pulling the hair into a straight shape. A flat iron was then applied to the hair at 400° F.

For all hair samples, a solution of hydrogen peroxide (2% v/v) was then applied to the hair until the hair was saturated, and the hair was allowed to sit for 30 minutes at room temperature. The hair was then rinsed with DI water.

The straightened hair was washed with shampoo and allowed to air dry. The break force of treated hair samples was measured using a custom apparatus. Individual hairs were cut into 13-centimeter-long sections. Both ends of the hairs were wrapped in tape 1 centimeter from each end. The hair was then held in a vertical position between two clamps (top=fixed, bottom =movable) with 1-centimeter-long grips such that the grips were aligned with the taped ends of the hair. Force was gradually applied to the bottom clamp, and the force at break was recorded. Ten replicates were collected for each treatment group.

Each hair sample was then washed with shampoo an additional 9 times and allowed to air dry. The break force for each hair sample was then remeasured following these additional washes using ten replicates for each sample.

Example 9: Measurement of Peptide Stability to Shampoo Washes

To separate solutions of 500 µL of DI water was added 1 mg of one of the peptides corresponding to SEQ ID NOs. 1 and 2-17. Then, a solution of 84 mg of sodium bicarbonate in 1 mL of DI water was prepared, and 12 µL of this solution was added to each peptide solution. Immediately prior to conjugation, 5 mg of Alexa Fluor 647 NHS ester (Thermo Fisher Scientific) dye molecule was dissolved in 500 µL of DMSO, and 15 µL of this solution was added to each peptide solution. After the dye was added, the solution was incubated at 4° C. in the dark for 16 hours. Removal of unbound dye molecules was carried out using a PD MiniTrap G-10 column (Cytiva) using DI water as the elutant. Fractions containing dye-labeled peptide were pooled and diluted to final peptide concentrations of 1 mg/mL.

Hair samples were then treated according to Example 8, except that during treatment with peptide, hair was treated with a single dye-labeled peptide corresponding to SEQ ID NOs. 1 and 2-17. For each set of conditions, three separate straightening protocols were performed.

Fluorescence images were collected on a EVOS M7000 Imaging System (Thermo Fisher Scientific) using a Cy5 filter set. Images were collected using a 0.1 second exposure time at a light intensity of 0.0023. Following fluorescence measurements, hair samples were then washed with shampoo an additional 9 times, towel dried, and fluorescently imaged again.

Image files were processed as 16-bit grayscale images using ImageJ software. A lower threshold of 497 intensity units was first applied to each image to remove background intensity from areas that did not contain hair strands. The average and standard deviation of fluorescence intensity in the remaining regions (corresponding to hair strands containing fluorescently labeled peptides) was then directly calculated.

Figure 9A:
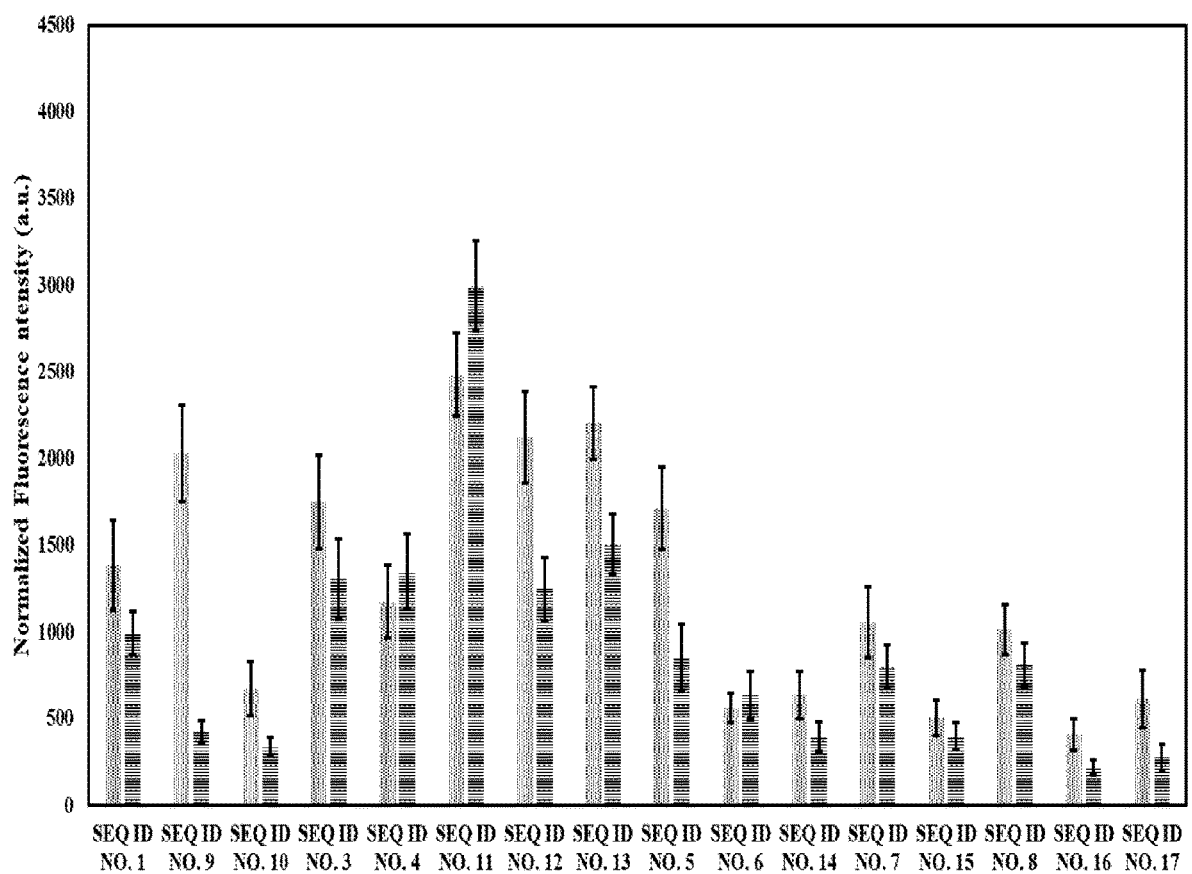
FIG. 9(a): Results of virgin hair after application of fluorescent peptide and shampooing 1 to 10 times as described in Example 9. Dotted bars represent the results after 1 shampoo, and bars with horizontal lines represent the results after 10 shampoos.
Figure 9B:
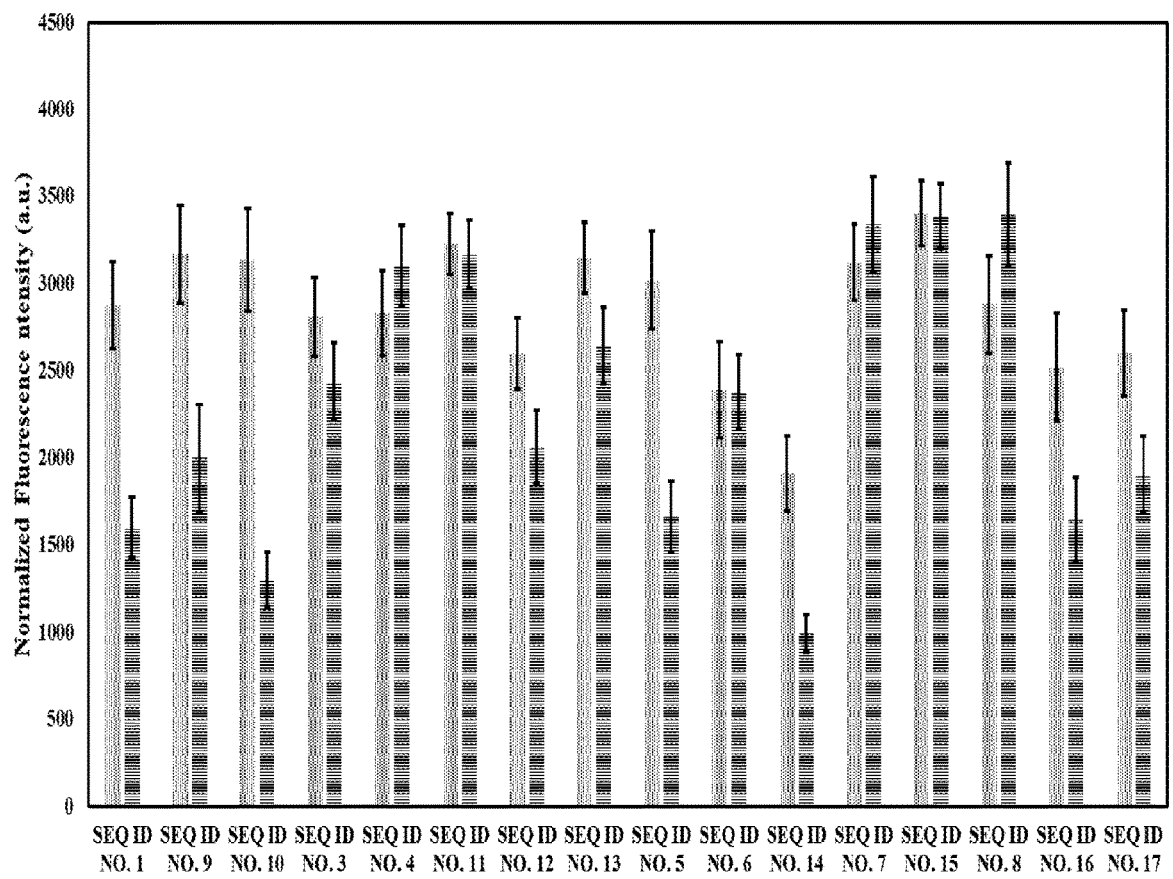
FIG. 9(b): Results of bleached hair after application of fluorescent peptide and shampooing 1 to 10 times as described in Example 9. Dotted bars represent the results after 1 shampoo, and bars with horizontal lines represent the results after 10 shampoos.
Figure 9C:
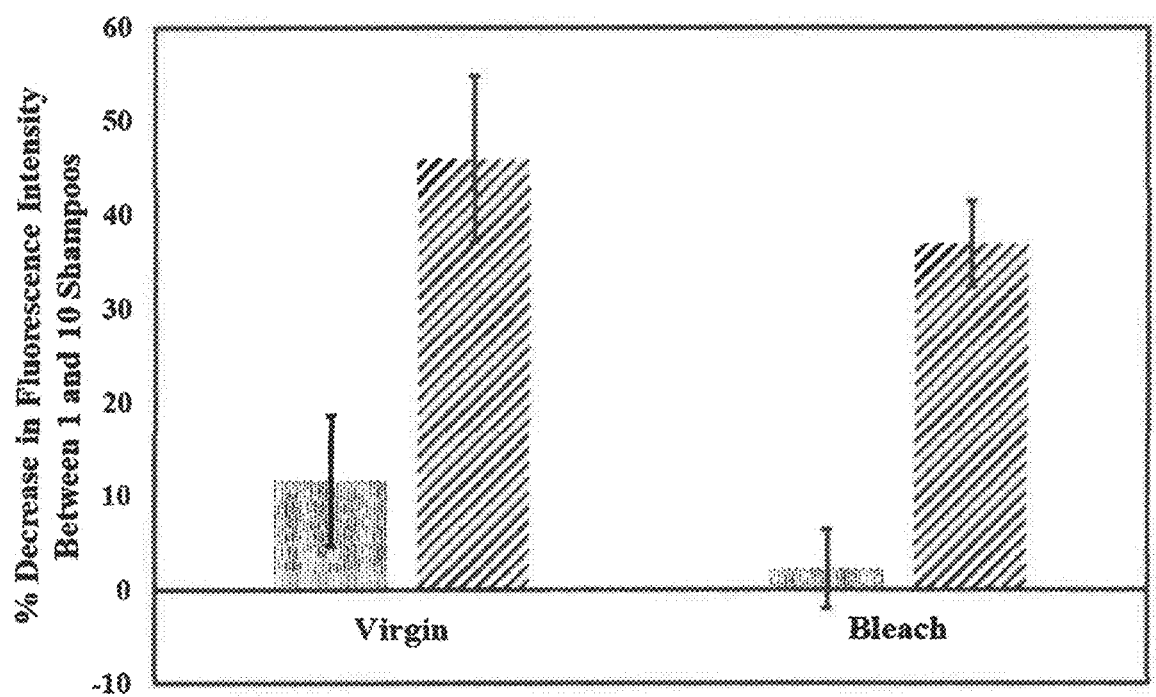
FIG. 9(c): Comparison of percent decrease in fluorescence intensity between 1 and 10 shampoos for peptides with and without Q13C substitution as described in Example 9. Dotted bars represent the results with the Q13C substitution, and bars with diagonal lines represent the results without the Q13C substitution.

Analysis of the peptides that showed strong resistance to shampoo washing, as indicated by no statistically significant decrease in fluorescence intensity between 1 and 10 shampoos in virgin (FIG. 9a) and bleached (FIG. 9b) hair, revealed that almost all of these peptides had a Q13C substitution relative to SEQ ID NO. 1. Indeed, peptides with this substitution showed a significantly smaller percentage loss from hair after 10 shampoo washes (FIG. 9c). Furthermore, SEQ ID NOs. 4, 11, 12, and 13 all have the Q13C substitution relative to SEQ ID NO. 1 and differ in sequence only by the number of other cysteine substitutions at common sites (3, 2, 1, and 0 additional cysteine substitutions, respectively). However, only hair treated with SEQ ID NOs. 4 and 11 shows no statistically significant decrease in fluorescence intensity between 1 and 10 shampoos, suggesting that a minimum of 2 non-Q13C cysteine substitutions may be required to allow the peptides to prevent loss from hair upon repeated shampooing. SEQ ID NOs. 14, 15, and 16 differ from SEQ ID NOs. 6, 7, and 8, respectively, in that the former sequences lack the Q13C substitutions found in the latter respective sequences. While hair treated with all of the latter peptides showed no statistically significant decrease in fluorescence intensity between 1 and 10 shampoos, SEQ ID NOs. 14 and 16 showed a significant decrease, generally supporting the importance of the Q13C substitution relative to SEQ ID NO. 1 in promoting strong binding to hair such that the peptide is not removed from hair during shampoo washes. The strong retention of SEQ ID NO.15 in hair through 10 shampoos despite lacking the Q13C substitution could suggest that the large number of cysteine substitutions in this peptide relative to SEQ ID NO.1 (10 cysteine substitutions) or the unique cysteine substitutions in this peptide, Q3C and/or Q8C, also allow strong binding to hair.

Example 10: Measurement of Retention in Hair for Library of Peptides following Shampoo Washes A 1 g sample of Brazilian hair was washed with 70% ethanol and incubated at room temperature in 20 mL of a 2:1 chloroform:methanol (v/v) solution for 16 hours to remove lipids from the hair. The hair was then thoroughly rinsed with DI water and added to a 20 mL solution of 100 mM Tris buffer pH 8.0 containing 8 M urea and 10% 2-mercaptoethanol (v/v). The hair was incubated at 50° C. for 5 days in this mixture, after which time the mixture was filtered. The filtrate was dialyzed against DI water at 4° C. using 8 exchanges with at least 3 hours between each exchange. The mixture was centrifuged at 10,000×g for 30 minutes at 4° C., the supernatant was collected, and the concentration of keratin proteins in the supernatant was measured using a BCA protein assay (Thermo Fisher Scientific).

The keratin mixture was diluted to a concentration of 5 mg/mL, and to 1 mL of this solution was added 60 µL of a solution of 84 mg of sodium bicarbonate in 1 mL of DI water. Immediately prior to conjugation, 1 mg of Alexa Fluor 647 NHS ester (Thermo Fisher Scientific) dye molecule was dissolved in 100 µL of DMSO, and 81 µL of this solution was added to the keratin solution. After the dye was added, the solution was incubated at 4° C. in the dark for 16 hours. Removal of unbound dye molecules was carried out using a PD MiniTrap G-10 column (Cytiva) using DI water as the elutant. Fractions containing dye-labeled keratin proteins were pooled.

A 4 mg sample of each of the 92 peptides corresponding to SEQ ID NOs. 18-109, which contained between 1 and 12 cysteine substitutions and between 0 and 4 alanine substitutions relative to SEQ ID NO. 1, was dissolved in 1 mL of DI water. A 50 µL sample of each solution was then added to a single well in 3 separate Nunc Covalink NH 96 well plates (Thermo Fisher Scientific), in which the wells are functionalized with free amines, such that three replicates could be obtained in future experiments. Then, 5.52 mg of N-hydroxysulfosuccinimide was dissolved in 15 mL of DI water, and 50 μL of this solution was added to each well. Then, 18.45 mg of N-(3-Dimethylaminopropyl)-N'-ethyl-carbodiimide hydrochloride was dissolved in 15 mL of DI water, and 50 μL of this solution was added to each well. The well plates were incubated at room temperature for 2 hours. Each well was then washed 5 times with DI water, using a 15-minute incubation time for the final wash.

Keratin proteins labeled with Alexa Fluor 647 was diluted to a concentration of 0.2 mg/mL in sodium hydroxide pH 10, and 80 μL of this solution was added to each well. The well plates were incubated for 1 hour at 37° C. Each well was then washed 5 times with DI water, using a 15-minute incubation time for the final wash. The wells were then incubated at room temperature with a 10% solution of shampoo for 5 minutes, washed 3 times with DI water, and allowed to air dry in the dark.

Fluorescence images were collected for each well in the three replicate well plates on a EVOS M7000 Imaging System (Thermo Fisher Scientific) using a Cy5 filter set. Images were collected using a 0.1 second exposure time at a light intensity of 0.15. Following fluorescence measurements, wells were subject to 9 additional cycles of 5 minutes incubations at room temperature in 10% shampoo. The wells were then washed 3 times with DI water, air dried in the dark, and fluorescently imaged again.

Figure 10A:
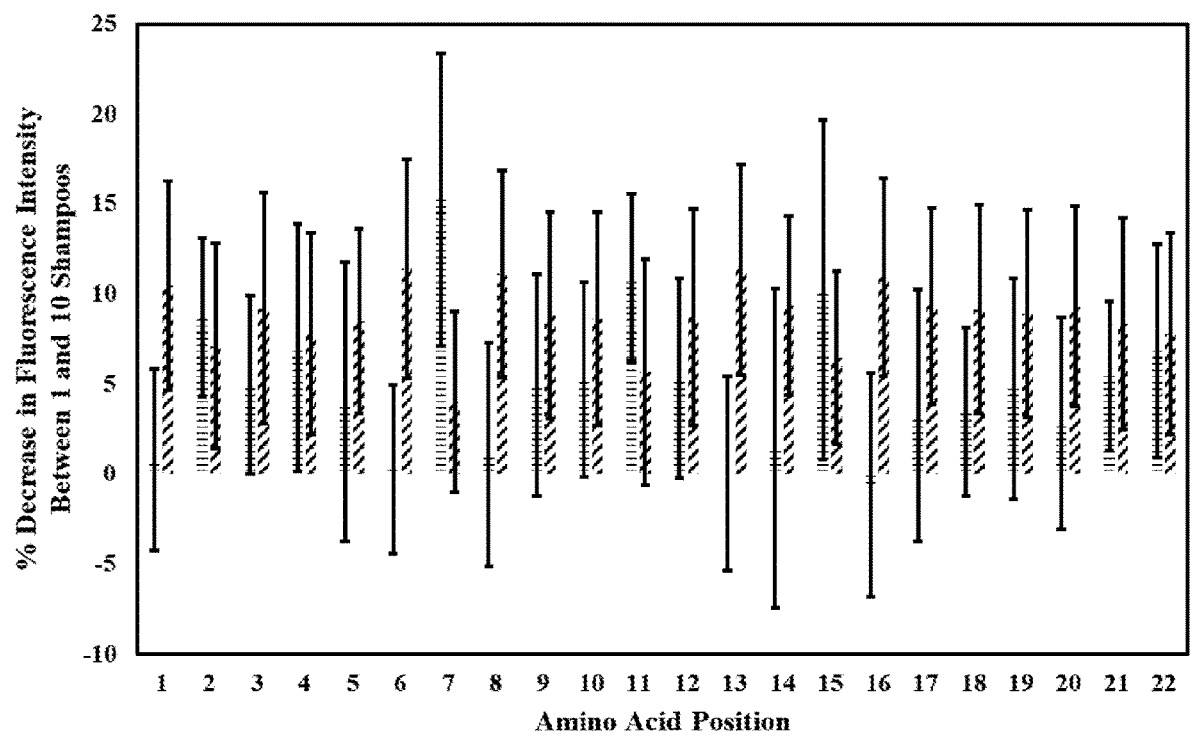
FIG. 10(a): Results of Example 10, demonstrating the percent decrease in fluorescence intensity between 1 and 10 shampoos for peptides that contain a cysteine substitution at the specified amino acid position (bars with horizontal lines) and peptides that do not contain a cysteine substitution at this position (bars with diagonal lines). Error bars represent a 95% confidence interval.
Figure 10:
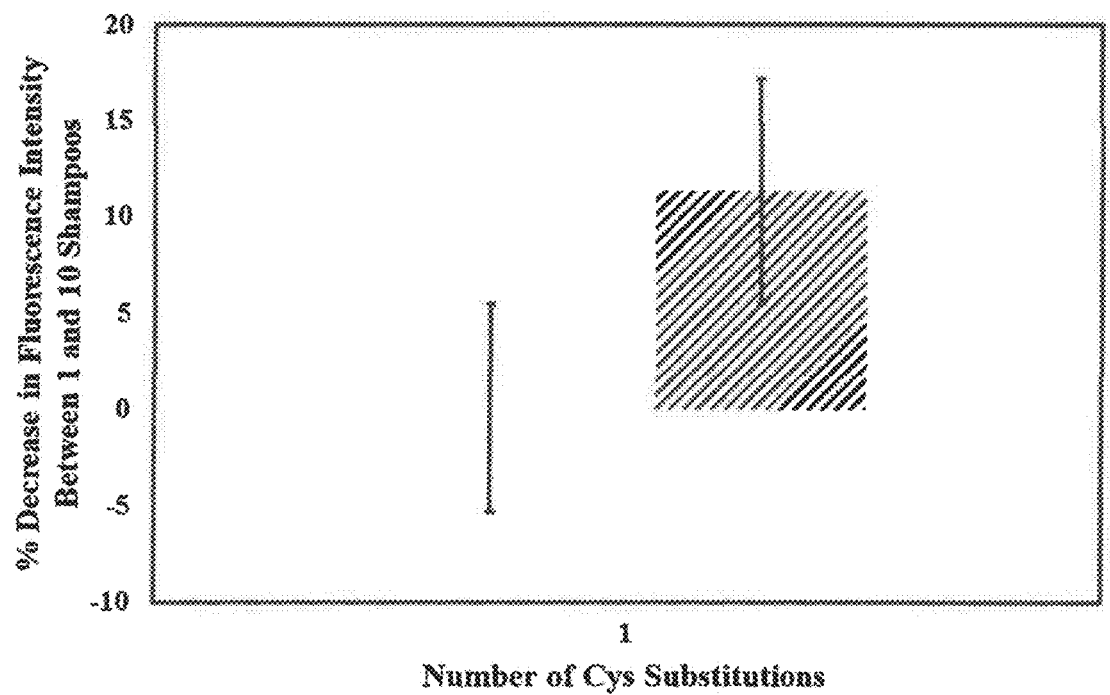
FIG. 10(b): Results of Example 10, demonstrating the percent decrease in fluorescence intensity between 1 and 10 shampoos for peptides that contain a Q13C substitution and a total number of cysteine substitutions greater than 1 (horizontal line) and peptides that either do not contain a Q13C substitution or have ≤1 substitutions (bar with diagonal lines). Error bars represent 95% confidence intervals.
FIG. 10(c): Results of Example 10, demonstrating the percent decrease in fluorescence intensity between 1 and 10 shampoos for peptides that contain a H6C substitution and a total number of cysteine substitutions greater than 1 (horizontal line) and peptides that either do not contain a H6C substitution or have ≤1 substitutions (bar with diagonal lines). Error bars represent 95% confidence intervals.
FIG. 10(d): Results of Example 10, demonstrating the percent decrease in fluorescence intensity between 1 and 10 shampoos for peptides that do not contain a Q13C or a H6C substitution and a total number of cysteine substitutions greater than the specified number of substitutions (bars with horizontal lines) and all other peptides from Example 10 (bars with diagonal lines). Error bars represent 95% confidence intervals.
Figure 10:
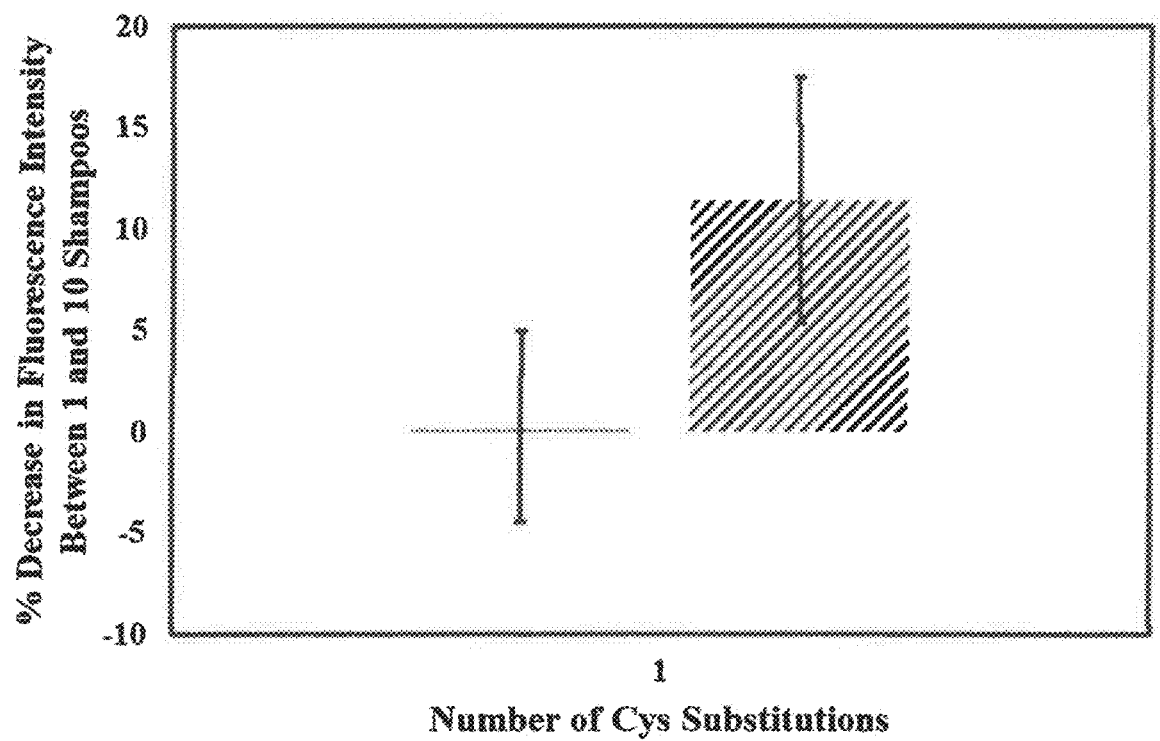
Figure 10:
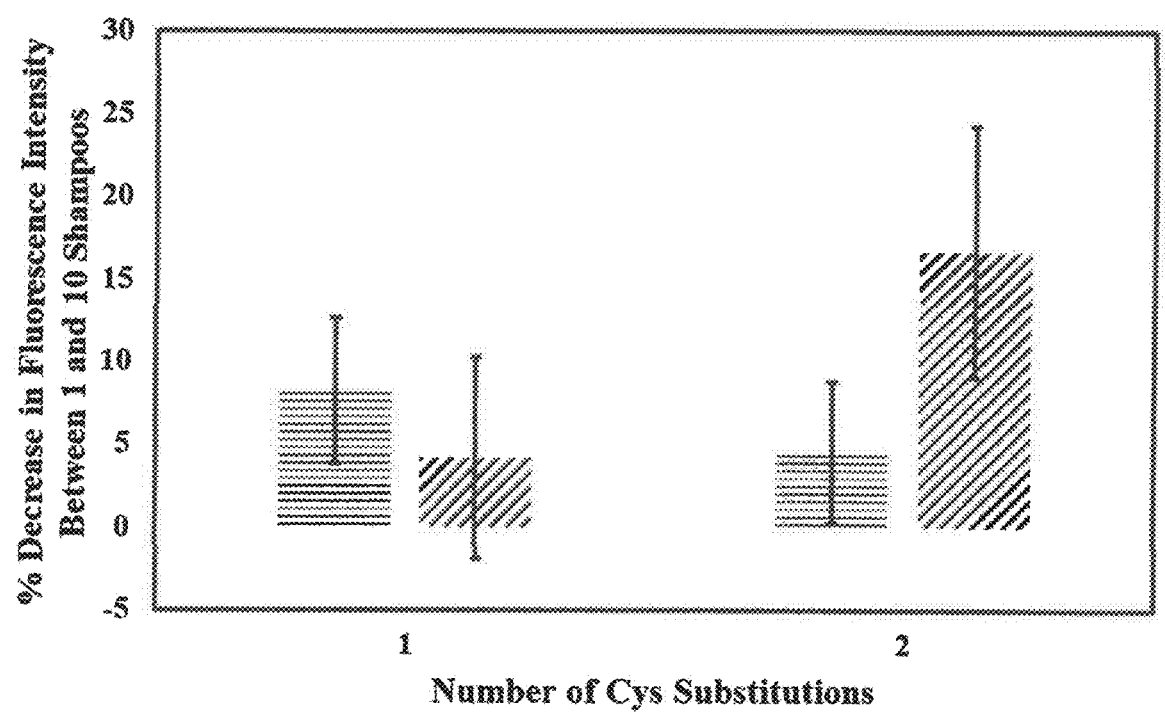

Analysis of the results demonstrated that peptides with either the Q13C or H6C substitutions showed significantly stronger binding against repeated shampoo washes than peptides without these substitutions (FIG. 10a). When the Q13C substitution was present in a peptide, at least 1 additional cysteine substitution was needed to observe a statistically significant improvement in resistance to shampoo washes (FIG. 10b). Similarly, when the H6C substitution was present in a peptide, at least 1 additional cysteine substitution was needed to observe a statistically significant improvement in resistance to shampoo washes (FIG. 10c). When neither the Q13C nor the H6C substitutions were present, peptides with 3 or more cysteine substitutions demonstrated significantly greater resistance to repeated shampoo washes than peptides with fewer than 3 cysteine substitutions or the Q13C and/or the H6C substitution (FIG. 10d).

What is claimed:

1. A method comprising:
applying to hair a composition comprising a plurality of a peptide comprising substitution of an at least one amino acid of SEQ ID NO:1 with a cysteine, wherein the peptide comprises at least 50% sequence identity to SEQ ID NO:1.

2. The method of claim 1, wherein the peptide comprises the amino acid sequence of any one of SEQ ID NO:8, SEQ ID NOS:3-7, or SEQ ID NOS:9-109, or a variant thereof with at least 70% sequence identity thereto.

3. The method of claim 1, wherein the cysteine substitution occurs at any one or more of a glutamine amino acid position, a valine amino acid position, an alanine amino acid position, and/or a serine amino acid position.

4. The method of claim 3, wherein the peptide comprises a Q13C substitution relative to amino acid sequence of SEQ ID NO:1.

5. The method of claim 3, wherein the peptide comprises an H6C substitution relative to amino acid sequence of SEQ ID NO:1.

6. The method of claim 3, wherein the peptide comprises a Q13C or H6C substitution and at least one additional cysteine substitution at any other amino acid position relative to SEQ ID NO:1.

7. The method of claim 6, wherein the at least one additional cysteine substitution is >1 and 11 amino acids relative to SEQ ID NO:1.

8. The method of claim 1, wherein the peptide comprises substitution of at least 3 amino acids of SEQ ID NO:1 with cysteine.

9. The method of claim 6, wherein the at least one additional cysteine substitution is >3 and <11 amino acids relative to SEQ ID NO:1.

10. The method of claim 2, wherein the peptide consists of the amino acid sequence of any one of SEQ ID NO:8, SEQ ID NOS: 3-7, or SEQ ID NOS:9-109.

11. The method of claim 1, wherein the peptide comprises 1 comprising the amino acid sequence of SEQ ID NO:8, or a variant thereof with at least 70% sequence identity thereto.

12. The method of claim 1, wherein a plurality of the peptides contacted with hair, optionally damaged hair, increases hair strength greater than the same number of peptides of SEQ ID NO:1 contacted with hair under the same conditions.

13. The method of claim 1, wherein the peptide binds keratin.

14. The method of claim 13, wherein a keratin-bound peptide is more resistant to washing than a keratin bound peptide consisting of the amino acid sequence of SEQ ID NO:1 contacted with hair under the same conditions.

15. The method of claim 1, wherein the composition is a liquid.

16. The method of claim 1 comprising about 0.01% to about 0.1% w/w of the peptide.

17. The method of claim 1, wherein the composition is selected from the group consisting of a shampoo, a conditioner, an oil, or a mask.

18. The method of claim 1, wherein the applying step occurs subsequent to application of a hair waving formulation, a hair straightening formulation, a hair coloring formulation, or a hair bleaching formulation to the hair.

19. The method of claim 1, wherein the peptide forms an alpha helix and at least one cysteine substitution is located on the outside region of the alpha helix.

20. The method of claim 1, wherein one cysteine substitution is located in the region of SEQ ID NO:1 consisting of SEQ ID NO:2.

21. The method of claim 20, wherein the one cysteine substitution located in the region of SEQ ID NO:1 consisting of SEQ ID NO:2 is a V17C substitution relative to the amino acid sequence of SEQ ID NO:1.

22. The method of claim 1, wherein during the applying step the composition is applied by hand, applicator bottle, applicator brush, dropper, or spray bottle.

23. The method of claim 1, wherein during the applying step the hair is saturated with the composition.

24. The method of claim 1, wherein following the applying step the hair is not washed for at least 24 hours.

25. The method of claim 1, wherein the peptide consists of the amino acid sequence of SEQ ID NO:8.

* * * * *